(12) United States Patent
Sato

(10) Patent No.: US 7,769,424 B2
(45) Date of Patent: Aug. 3, 2010

(54) INTERCEREBRAL CURRENT SOURCE ESTIMATION METHOD INTERCEREBRAL CURRENT SOURCE ESTIMATION PROGRAM RECORDING MEDIUM CONTAINING THE INTERCEREBRAL CURRENT SOURCE ESTIMATION PROGRAM AND INTERCEREBRAL CURRENT SOURCE ESTIMATION APPARATUS

(75) Inventor: Masa-aki Sato, Kyoto (JP)

(73) Assignees: Japan Science and Technology Agency, Saitama (JP); Advanced Telecommunications Research Institute International, Kyoto (JP)

( * ) Notice: Subject to any disclaimer, the term of this patent is extended or adjusted under 35 U.S.C. 154(b) by 1718 days.

(21) Appl. No.: 10/500,369
(22) PCT Filed: Dec. 27, 2002
(86) PCT No.: PCT/JP02/13739

§ 371 (c)(1),
(2), (4) Date: Jun. 28, 2004

(87) PCT Pub. No.: WO03/057035

PCT Pub. Date: Jul. 17, 2003

(65) Prior Publication Data

US 2005/0020933 A1 Jan. 27, 2005

(30) Foreign Application Priority Data

Dec. 28, 2001 (JP) ............................. 2001-400519

(51) Int. Cl.
*A61B 5/05* (2006.01)
(52) U.S. Cl. .................. 600/409; 600/407; 600/410; 600/414; 378/62; 378/54
(58) Field of Classification Search ................. 600/407, 600/410, 409, 414, 418, 421, 425, 436, 544, 600/545, 547, 562, 372, 382, 384, 386, 461, 600/476, 477, 478; 378/62, 54, 19, 145, 378/146
See application file for complete search history.

(56) References Cited

U.S. PATENT DOCUMENTS

| 6,014,582 A | 1/2000 | He |
| 6,330,470 B1 | 12/2001 | Tucker et al. |

(Continued)

FOREIGN PATENT DOCUMENTS

| EP | 0 315 545 A1 | 5/1989 |
| JP | 10-211181 | 8/1998 |
| JP | 11-313807 | 11/1999 |

OTHER PUBLICATIONS

Baillet et al. "A Bayesian Approach to Intorducing Anatomo-Functional Priors in the EEG/MEG Inverse Problem", May 1997, IEE Transactions on Biomedical Engineering, vol. 44, No. 5, pp. 374-385.*

(Continued)

*Primary Examiner*—Brian Casler
*Assistant Examiner*—Nasir Shahrestani
(74) *Attorney, Agent, or Firm*—McDermott Will & Emery LLP

(57) ABSTRACT

Based on the fact that by causing an appropriate current flow on a virtual curved surface between a current source and an observation surface, an electromagnetic field generated by the current source can be recovered, and that as the curved surface comes closer to the true current source, current distribution on the curved surface becomes smaller, Bayesian estimation of the current source that recovers the observed data is performed. In this estimation, the fact that the model posterior probability attains the maximum when the curved surface includes the current source is utilized, that is, the model posterior probability is considered, to estimate the position of the current source including the depth direction. When observation data obtained by other observation means is available simultaneously, such information is incorporated in hierarchical prior distribution for Bayesian estimation, to enable estimation with higher precision.

15 Claims, 33 Drawing Sheets

U.S. PATENT DOCUMENTS

| | | | |
|---|---|---|---|
| 6,594,521 B2* | 7/2003 | Tucker | 600/544 |
| 7,092,748 B2* | 8/2006 | Valdes Sosa et al. | 600/407 |
| 2003/0081818 A1* | 5/2003 | Fujimaki | 382/128 |
| 2003/0093005 A1* | 5/2003 | Tucker | 600/544 |

OTHER PUBLICATIONS

Baillet et al. "A Bayesian Approach to Intorducing Anatomo-Functional Priors in the EEG/MEG Inverse Problem", May 1997, IEEE Transactions on Biomedical Engineering, vol. 44, No. 5, pp. 374-385.*

Masaaki Sato, "Henbun Bayesian-Ho Ni Yoru MEG Dengen Suitei", The Institute of Electronics, Information and Communication Engineers Gijutsu Kenkyu Hokoku, Mar. 12, 2002. vol. 101, No. 736, pp. 167-174.

Gerald S. Russell, Ramsch Srinivasan and Don M. Tucker, Bayesian Estimates of Error Bounds for EEG Source Imaging, IEEE Transactions on Medical Imaging, 1998, vol. 17, No. 6, pp. 1084-1089.

James W. Phillips, Richard M. Leahy and John C. Mosher, MEG-Based Imaging of Focal Neuronal Current Sources, IEEE Transactions on Medical Imaging, 1997, vol. 16, No. 3, pp. 338-348.

J.C. Mosher, P.S. Lewis, and R.M. Leahy, "Multiple Dipole Modeling and Localization From Spatio-Temporal MEG Data", IEEE Transactions on Biomedical Engineering, vol. 39, No. 6, pp. 541-557, Jun. 1992.

K. Toyama, K. Yoshikawa, Y. Yoshida, Y. Kondo, S. Tomita, Y. Takanashi, Y. Ejima, and S. Yoshizawa, "A New Method for Magnetoencephalography: A Three-Dimensional Magnetometer-Spatial Filter System", Neuroscience vol. 91, No. 2, pp. 405-415, 1999.

R.M. Neal, "Bayesian Learning for Neural Networks", Springer Verlag, 1996.

H. Attias, "Inferring Parameters and Structure of Latent Variable Models by Variational Bayes", Proceedings of the Fifteenth Conference on Uncertainty in Artificial Intelligence, pp. 21-30, 1999.

Masa-aki Sato, "Online Model Selection Based on the Variational Bayes", Neural Computation, 13, 1649-1681, 2001.

J. Sarvas, "Basic Mathematical and Electromagnetic Concepts of the Biomagnetic Inverse Problem", Phys. Med. Biol., vol. 32, No. 1, pp. 11-22, 1987.

M.S. Hamalainen and R.J. Ilmoniemi, "Interpreting Magnetic Fields of the Brain: Minimum Norm Estimates", Medical & Biological Engineering & Computing, 32, pp. 35-42, 1994.

A.M. Dale et al., "Dynamic Statistical Parametric Mapping: Combining fMRI and MEG for High-Resolution Imaging of Cortical Activity", Neuron, vol. 26, pp. 55-67, 2000.

Canadian Office Action, issued in corresponding Canadian Patent Application No. 2,471,746, dated on Jul. 13, 2007.

Baillet et al. "A Bayesian Approach to Introduction Anatomo-Functional Priors in the EEG/MEG Inverse Problem", IEEE Transactions on Biomedical Engineering, vol. 44, No. 5, May 1997, pp. 374-385.

European Search Report issued in European Patent Application No. EP 02793435.5-1265/1468647 PCT/JP0213739, dated Jun. 23, 2009.

He, Bin, "High-Resolution Source Imaging of Brain Electrical Activity: Enhancing Spatial Resolution with Cortical Imaging," IEEE Engineering in Medicine and Biology, Sep./Oct. 1998, pp. 123-129.

Gavit, Laurence et al., "A Multiresolution Framework to MEG/EEG Source Imaging," IEEE Transactions on Biomedical Engineering, vol. 48, No. 10 Oct. 2001, pp. 1080-1087.

Kralik, J. et al., "Head Reconstruction and Localization of Brain Activity Using Bayesian Evidence," 2001 Proceedings of the 23rd Annual EMBS International Conference, Oct. 25-28, Istanbul, Turkey, 2001, pp. 1940-1943.

* cited by examiner

R=5.0

R=6.0

R=7.0

R=5.0

R=6.0

R=7.0

INTERCEREBRAL CURRENT SOURCE ESTIMATION METHOD INTERCEREBRAL CURRENT SOURCE ESTIMATION PROGRAM RECORDING MEDIUM CONTAINING THE INTERCEREBRAL CURRENT SOURCE ESTIMATION PROGRAM AND INTERCEREBRAL CURRENT SOURCE ESTIMATION APPARATUS

TECHNICAL FIELD

The present invention relates to a method of estimating position or distribution of a brain current source or sources generating magnetic fields or electric fields outside a scalp in correspondence to brain activities, as well as to a brain current source estimating program, a recording medium recording the brain current source estimating program and to a brain current source estimating apparatus.

BACKGROUND ART

Thanks to remarkable development in the field of biomedical measurement technique, precision in measuring weak electric field (brain wave) or weak magnetic field (brain magnetic wave) generated from the brain, of which measurement has been difficult and error-prone, has been improved year by year.

Specifically, receiving external stimuli, neural cells in the brain generate a current. The current results in the aforementioned weak electric field or weak magnetic field. Here, "brain wave" refers to the electric field generated from the brain by the current from the neural cells. An "electroencephalogram: EEG" refers to a method of measuring the brain wave.

The "brain magnetic wave" refers to a magnetic field generated from the brain by the current from the neural cells. A "magnetoencephalography: MEG" refers to a method of measuring the brain magnetic wave. A crucial advantage of the magnetoencephalography is that, as the magnetic field is almost free of any influence of volume conductor, it is expected that relatively accurate three-dimensional estimation of the position of a brain current source can be attained by measuring magnetism from outside one's scalp.

In the analysis of the brain magnetic wave, an active portion of the brain is estimated in a non-invasive manner, by measuring the generated magnetic field from outside the brain.

The magnetic field, however, is so weak that it is very susceptible to the influence of external magnetic field such as terrestrial magnetism. Therefore, the weak magnetic field is measured by a Superconducting QUantum Interference Device (SQUID), which is a measuring device utilizing superconductivity, within a shield that shuts out any external magnetic field.

It is noted, however, that in the field of studying algorithms for "estimating positions of brain current source," decisive method is non-existent at present, though various and many variations of initial models have been tried.

By way of example, "dipole estimation method" as one algorithm for "estimating positions of brain current sources," is disclosed in Reference 1: J. C. Mosher, P. S. Lewis and R. M. Leahy, IEEE Trans. Biomed. Engng. <1992> vol. 39, pp.541-557. In the "dipole estimation method," however, the position of a dipole is estimated from observed magnetic field, assuming that the current source in the brain can be represented by one or a number of current dipoles, and this method is disadvantageous in that it is difficult to determine the number of dipoles.

As another algorithm, "spatial filtering method" is disclosed in Reference 2: K. Toyama, K. Yoshikawa, Y. Yoshida, Y. Kondo, S. Tomita, Y. Takanashi, Y. Ejima and S. Yoshizawa, Neuroscience, 1999, 91 (2), pp. 405-415. In the "spatial filtering method," location of a brain current source is restricted in consideration of physiological findings, and distribution of dipoles is estimated. This method is disadvantageous in that accurate estimation of the depth of the current source is not possible.

DISCLOSURE OF THE INVENTION

An object of the present invention is to provide a brain current source estimating method that enables estimation of a position, depth direction inclusive, of a brain current source.

Another object of the present invention is to provide a brain current source estimating method that enables estimation of positions of a plurality of brain current sources from observed data, even when there are a plurality of brain current sources.

A still further object of the present invention is to provide a brain current source estimating method enabling estimation with higher accuracy, when observation data obtained by a method of observation independent of the observation of magnetic field for estimating the brain current source are available, by combining data obtained by the plurality of observation methods.

A still further object of the present invention is to provide a brain current source estimating program that enables estimation of a position, depth direction inclusive, of a brain current source and a recording medium having the program recorded thereon.

A still further object of the present invention is to provide a brain current source estimating program that enables estimation of positions of a plurality of brain current sources from observed data, even when there are a plurality of brain current sources, and a recording medium having the program recorded thereon.

A still further object of the present invention is to provide a brain current source estimating program enabling estimation with higher accuracy, when observation data obtained by a method of observation independent of the observation of magnetic field for estimating the brain current source are available, by combining data obtained by the plurality of observation methods, and a recording medium having the program recorded thereon.

A still further object of the present invention is to provide a brain current source estimating apparatus that enables estimation of a position, depth direction inclusive, of a brain current source.

A still further object of the present invention is to provide a brain current source estimating apparatus that enables estimation of positions of a plurality of brain current sources from observed data, even when there are a plurality of brain current sources.

A still further object of the present invention is to provide a brain current source estimating apparatus enabling estimation with higher accuracy, when observation data obtained by a method of observation independent of the observation of magnetic field for estimating the brain current source are available, by combining data obtained by the plurality of observation methods.

In order to attain the above described objects, the present invention provides a brain current source estimating method for estimating, based on an electromagnetic field observed outside a scalp, a position of a current source as a source of the electromagnetic wave existing in the brain, including the steps of: setting, in the brain, a plurality of virtual curved surfaces having depths from brain surface different from each other and shapes not intersecting with each other and setting lattice points on each of the virtual curved surfaces; estimating, on each of the virtual curved surfaces, a current distribution for recovering the observed electromagnetic field; and based on an expansion of the current distribution estimated on the virtual curved surfaces and a difference between the electromagnetic field recovered based on the current distribution and the observed electromagnetic field, identifying a virtual curved surface at which the expansion and the difference attain relative minimums among the plurality of virtual curved surfaces as a true curved surface on which the current source exists.

Preferably, the step of estimating the current distribution includes the step of determining posterior probability by Bayesian estimation method from prior distribution and observation data of the electromagnetic field; and the step of identifying as a true curved surface on which the current source exists includes the step of identifying a virtual curved surface of which corresponding posterior probability attains the highest, among the virtual curved surfaces.

Preferably, the step of estimating a current distribution includes the step of identifying a first virtual curved surface closest to the brain surface and having posterior probability attaining a relative maximum, among the plurality of virtual surfaces, while successively moving from a virtual curved surface on the side of the brain surface to a deeper side; and the step of identifying a curved surface as a true curved surface on which the current source exists includes the steps of identifying a localized current distribution corresponding to a point of relative maximum of the current distribution, on the first virtual curved surface, separating a plurality of local surfaces each including the localized current distribution, and fixing, among the plurality of local surfaces, local surfaces other than a local surface as an object of identification, moving the local surface as an object of identification in the depth direction, and identifying positions where the posterior probability attains the relative maximum, successively from the side closer to the brain surface.

Preferably, in the step of estimating a current distribution, the current distribution is estimated with a first spatial resolution; and the method further includes the step of re-estimating the current distribution with a second spatial resolution higher than the first resolution and resolution of the plurality of virtual curved surfaces in the depth direction being improved.

Preferably, the step of estimating a current distribution includes the step of setting, when the current distribution is estimated in accordance with Bayesian estimation, a hierarchical prior distribution in the Bayesian estimation using observation data obtained by other observation method independent of the observation of electromagnetic field for the estimation of the current source. By way of example, when it is known from observation data obtained by a different method of observation that the location of the brain current source is within a restricted area, search in the depth direction may be omitted and the current distribution in the restricted area can be obtained by Bayesian estimation.

According to another aspect, the present invention provides a program for a computer for estimating, based on an electromagnetic field observed outside a scalp, a position of a current source as a source of the electromagnetic wave existing in the brain, to have the computer execute the steps of: setting, in the brain, a plurality of virtual curved surfaces having depths from brain surface different from each other and shapes not intersecting with each other and setting lattice points on each of the virtual curved surfaces; estimating, on each of the virtual curved surfaces, a current distribution for recovering the observed electromagnetic field; and based on an expansion of the current distribution estimated on the virtual curved surfaces and a difference between the electromagnetic field recovered based on the current distribution and the observed electromagnetic field, identifying a virtual curved surface at which the expansion and the difference attain relative minimums among the plurality of virtual curved surfaces as a true curved surface on which the current source exists.

Preferably, the step of estimating the current distribution includes the step of determining posterior probability by Bayesian estimation method from prior distribution and observation data of the electromagnetic field; and the step of identifying as a true curved surface on which the current source exists includes the step of identifying a virtual curved surface of which corresponding posterior probability attains the highest, among the virtual curved surfaces.

Preferably, the step of estimating a current distribution includes the step of identifying a first virtual curved surface closest to the brain surface and having posterior probability attaining a relative maximum, among the plurality of virtual surfaces, while successively moving from a virtual curved surface on the side of the brain surface to a deeper side; and the step of identifying a curved surface as a true curved surface on which the current source exists includes the steps of identifying a localized current distribution corresponding to a point of relative maximum of the current distribution, on the first virtual curved surface, separating a plurality of local surfaces each including the localized current distribution, and fixing, among the plurality of local surfaces, local surfaces other than a local surface as an object of identification, moving the local surface as an object of identification in the depth direction, and identifying positions where the posterior probability attains the relative maximum, successively from the side closer to the brain surface.

Preferably, in the step of estimating a current distribution, the current distribution is estimated with a first spatial resolution; and the method further includes the step of re-estimating the current distribution with a second spatial resolution higher than the first resolution and resolution of the plurality of virtual curved surfaces in the depth direction being improved.

Preferably, the step of estimating a current distribution includes the step of setting, when the current distribution is estimated in accordance with Bayesian estimation, a hierarchical prior distribution in the Bayesian estimation using observation data obtained by other observation method independent of the observation of electromagnetic field for the estimation of the current source. By way of example, when it is known from observation data obtained by a different method of observation that the location of the brain current source is within a restricted area, search in the depth direction may be omitted and the current distribution in the restricted area can be obtained by Bayesian estimation.

According to a still further aspect, the present invention provides a brain current source estimating apparatus for estimating, based on an electromagnetic field observed outside a scalp, a position of a current source as a source of the electromagnetic wave existing in the brain, including: virtual curved surface setting means for setting, in the brain, a plurality of virtual curved surfaces having depths from brain surface different from each other and shapes not intersecting with each other and setting lattice points on each of the virtual curved surfaces; current distribution estimating means for estimating, on each of the virtual curved surfaces, a current distribution for recovering the observed electromagnetic field; and current source identifying means for identifying, based on an expansion of the current distribution estimated on the virtual curved surfaces and a difference between the electromagnetic field recovered based on the current distribution and the observed electromagnetic field, a virtual curved surface at which the expansion and the difference attain relative minimums among the plurality of virtual curved surfaces as a true curved surface on which the current source exists.

Preferably, the current distribution estimating means includes posterior probability determining means for determining posterior probability by Bayesian estimation method from prior distribution and observation data of the electromagnetic field; and the current source identifying means includes virtual curved surface identifying means for identifying a virtual curved surface of which corresponding posterior probability attains the highest, among the virtual curved surfaces.

Preferably, the current distribution estimating means includes shallowest virtual curved surface identifying means for identifying a first virtual curved surface closest to the brain surface and having posterior probability attaining a relative maximum, among the plurality of virtual surfaces, while successively moving from a virtual curved surface on the side of the brain surface to a deeper side; and the current source identifying means includes localized current distribution identifying means for identifying a localized current distribution corresponding to a point of relative maximum of the current distribution, on the first virtual curved surface, local surface extracting means for separating a plurality of local surfaces each including the localized current distribution, and local surface position identifying means for fixing, among the plurality of local surfaces, local surfaces other than a local surface as an object of identification, moving the local surface as an object of identification in the depth direction, and identifying positions where the posterior probability attains the relative maximum, successively from the side closer to the brain surface.

Preferably, the current distribution estimating means estimates the current distribution with a first spatial resolution and thereafter re-estimates the current distribution with a second spatial resolution higher than the first resolution and resolution of the plurality of virtual curved surfaces in the depth direction being improved.

Preferably, the current distribution estimating means includes means for setting, when the current distribution is estimated in accordance with Bayesian estimation, a hierarchical prior distribution in the Bayesian estimation using observation data obtained by other observation method independent of the observation of electromagnetic field for the estimation of the current source. By way of example, when it is known from observation data obtained by a different method of observation that the location of the brain current source is within a restricted area, search in the depth direction may be omitted and the current distribution in the restricted area can be obtained by Bayesian estimation.

According to the brain current source estimating method of the present invention, it is possible to estimate the position of a brain current source including the depth direction, from observation data of MEG or EEG. Such estimation in the depth direction is applicable even when there are a plurality of current sources. Further, the method is applicable where the current sources exist locally as in the case of current dipoles and applicable to a current source that has a certain expansion. Further, it is possible to estimate how the current source expands.

BEST MODES FOR CARRYING OUT THE INVENTION

Embodiments of the present invention will be described with reference to the figures.

As already described, magnetoencephaography: MEG and electroencephalogram: EEG have been known as methods of monitoring brain activities from the outside. In the following, description will be given mainly focusing on MEG. It is noted, however, that the present invention is also applicable to EEG, when the magnetic field in MEG is replaced by the electric field.

The term "electromagnetic field" originally refers to co-existence of "electric field" and "magnetic field." In the present specification, however, an expression "observe an electromagnetic field" will be used generally, where the physical amount "to be observed" is an "electric field" or a "magnetic field."

[First Embodiment]

Figure 1:
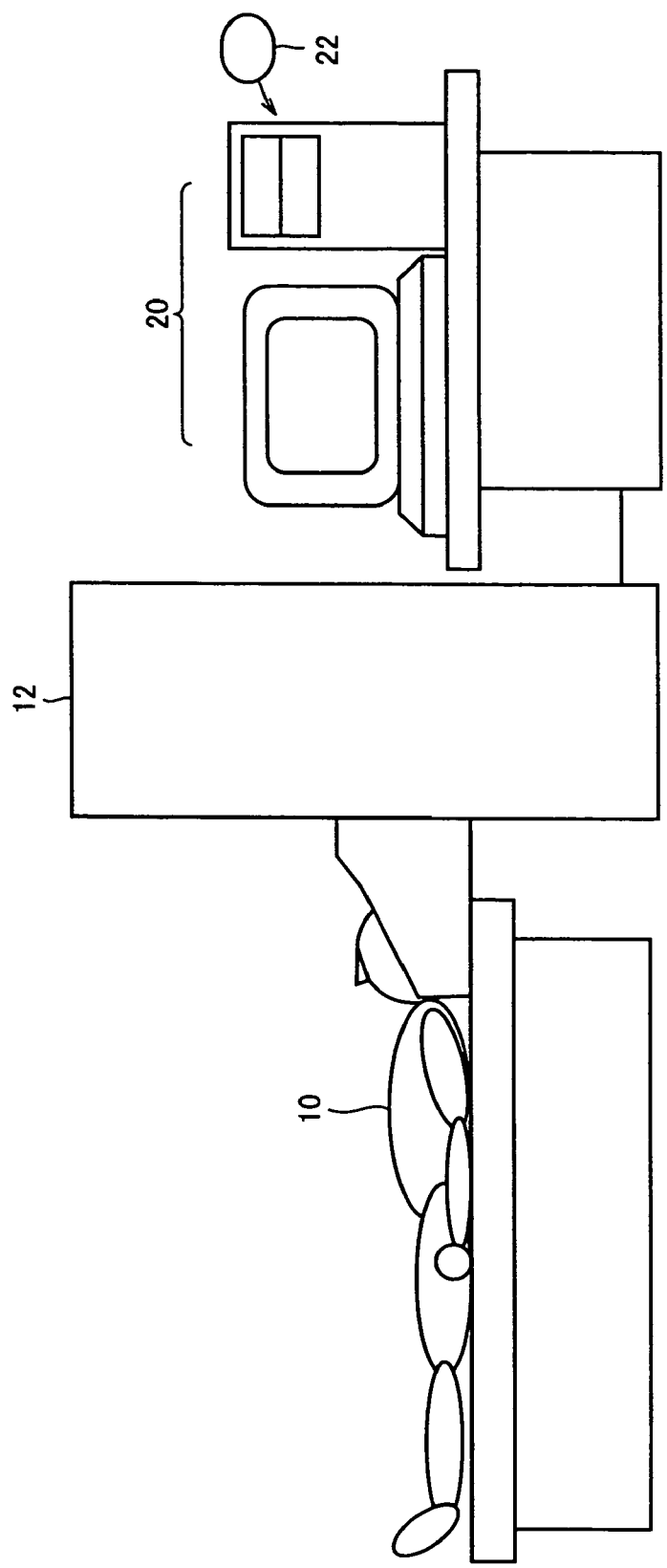
FIG. 1 is a schematic illustration of an exemplary configuration of an MEG system.

FIG. 1 is a schematic illustration of an exemplary configuration of an MEG system.

An MEG 12 includes an array of multi-channel SQUID flux meter (super sensitive magnetometer), for measuring a magnetic field on the scalp surface of a subject 10. Receiving the result of measurement by MEG 12, a computer system 20 analyses the result of measurement, and performs a process for estimating the position of a brain current source.

The present invention relates to software processing by computer system 20. It is noted, however, that part of or all of the process may be performed by hardware to increase the speed of processing. The software is not specifically limited, and it may be recorded on a recording medium 22 such as a CD-ROM (Compact Disk Read Only Memory) or a DVD-ROM-(Digital Versatile Disc Read Only Memory) and installed in computer system 20, or it may be distributed through a communication network.

[Principle of Brain Current Source Estimation]

Prior to detailed description of the "brain current source estimating method" in accordance with the present invention, the principle and outline of the estimation method of the present invention will be summarized.

(Recovery of Electromagnetic Field by Current Distribution on a Curved Surface)

It is well-known as the principle of electromagnetic shield that when a current source is surrounded by an ideal electromagnetic shielding surface formed of metal and magnetic body, electromagnetic field cease to exist outside the shielding surface. Specifically, by the electromagnetic field formed by the current flowing over the shielding surface and a collection of small magnets constituting the magnetic body, the electromagnetic field formed by the current source outside the shielding surface is fully cancelled. Further, the small magnets can be replaced by a virtual eddy current. When viewed from a different point, this means that an electromagnetic field identical to that formed by the current source can be formed outside the shielding surface by causing an appropriate current flow over the shielding surface. On the contrary, the electric field outside the shielding surface cannot be fully recovered, whatever current is caused to flow over the shielding surface. This fact will be referred to as the "principle of electromagnetic field recovery."

Figure 2:
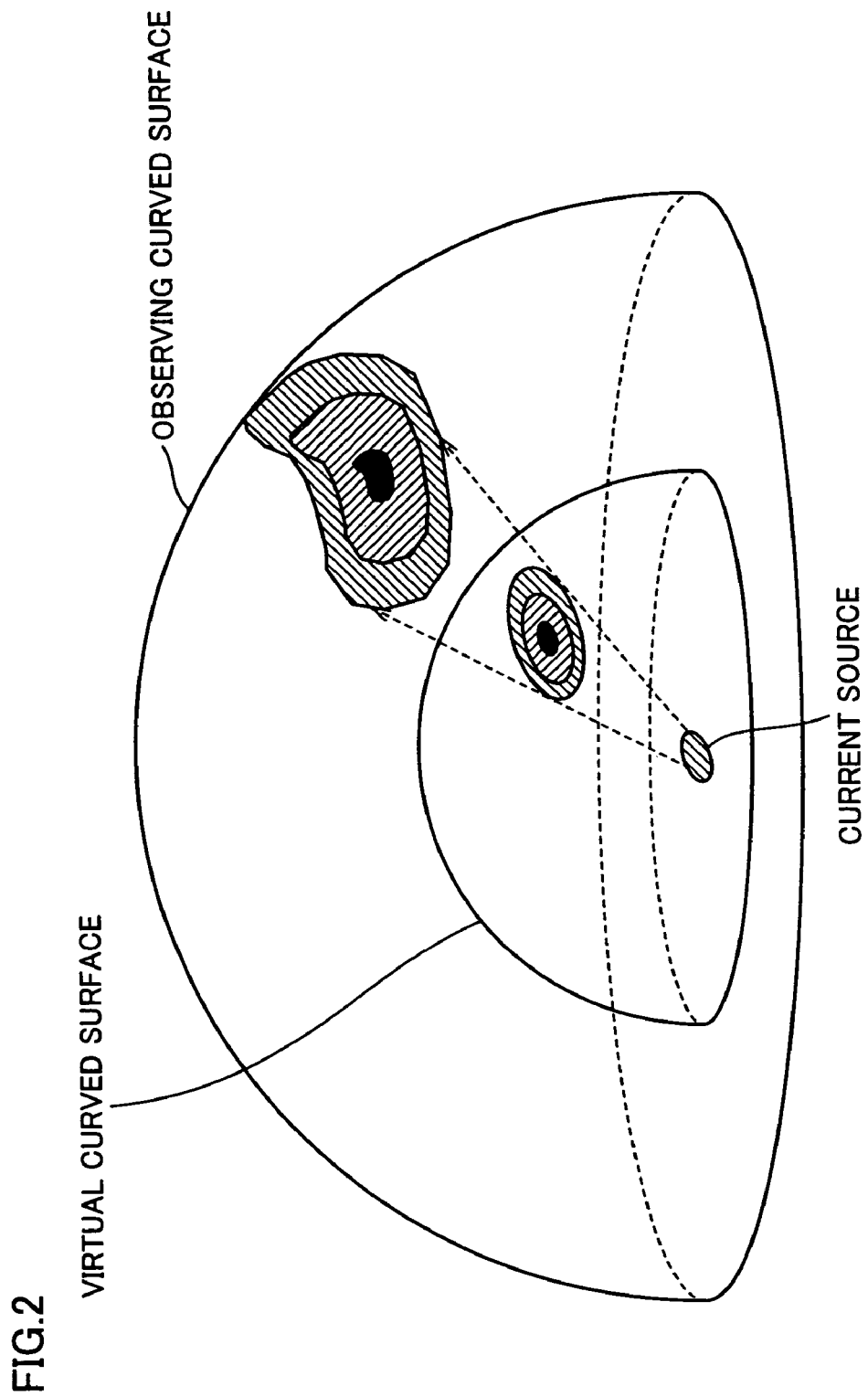
FIG. 2 is a schematic illustration representing a magnetic field generated by a current source, observed on an appropriate curved surface.

FIG. 2 is a schematic illustration representing a magnetic field generated by a current source, observed on an appropriate curved surface.

As can be seen from FIG. 2, when a virtual surface is prepared between an observing surface and the current source, it is possible to recover the electromagnetic field formed by the current source on the observing surface by causing an appropriate flow of current on the virtual surface, in accordance with the "principle of electromagnetic field recovery."

Figure 3:
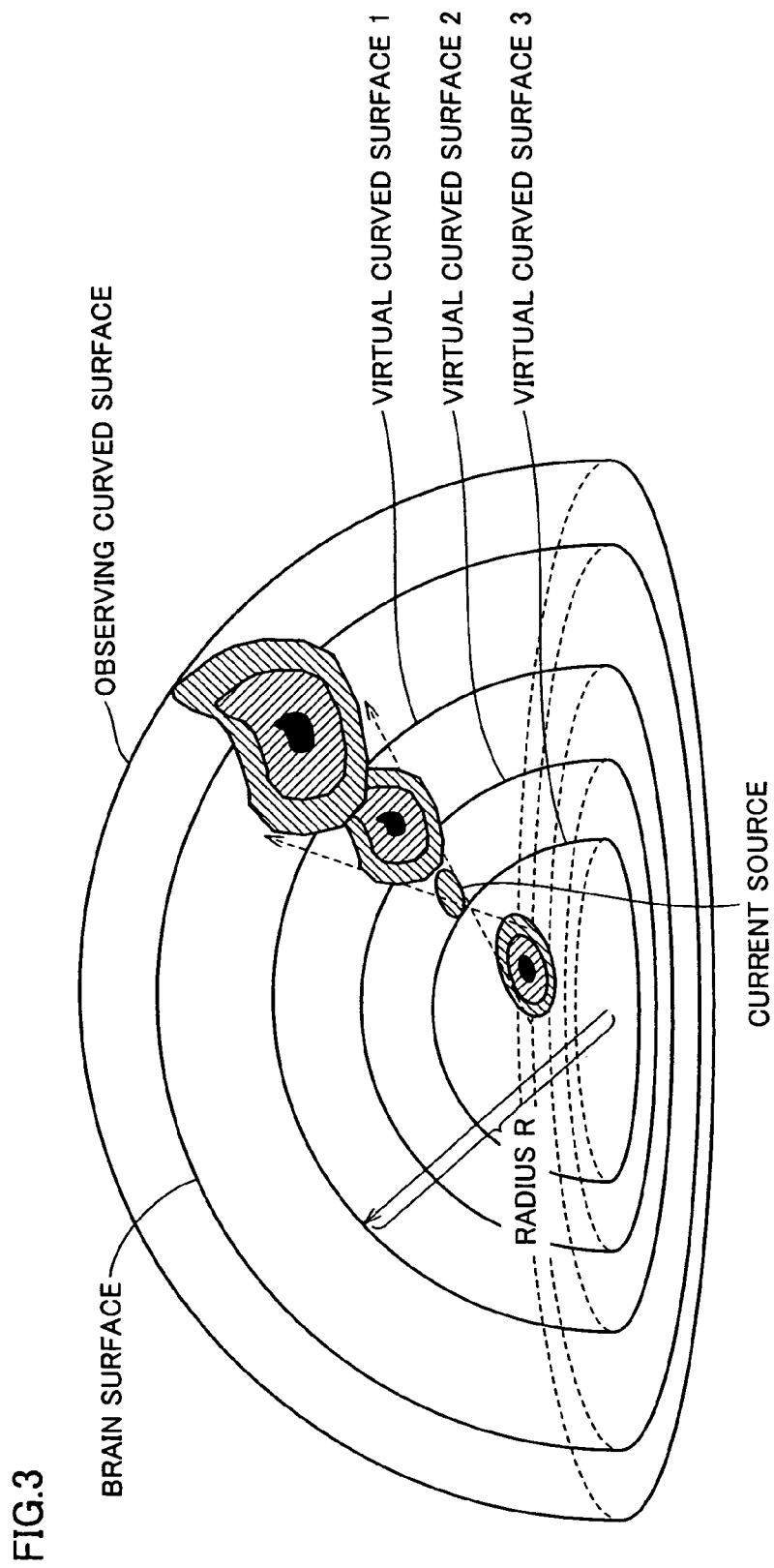
FIG. 3 is a schematic illustration representing a relation between a current source in the brain and a plurality of virtual curved surfaces.

FIG. 3 is a schematic illustration representing a relation between a current source in the brain and a plurality of virtual curved surfaces.

Referring to FIG. 3, considering that the electromagnetic field formed by the current attenuates in inverse proportion to the square of distance, the expansion of current on the virtual curved surface (virtual curved surface 2) equivalent to the current source becomes wider as the virtual surface is further away from the current source. Therefore, the expansion of the current on virtual curved surface 1 is wider than that on virtual curved surface 2.

On a virtual curved surface (virtual curved surface 3) on the side opposite to the observing surface with respect to the current source, it is impossible to fully recover the electromagnetic field formed on the observing surface by the current source.

According to the present invention, based on the principle described above, the current source is estimated from the observed data of the electromagnetic field on the observing surface.

(Principle of Current Source Estimation)

Assume that a magnetic field (or an electric field) formed by a current source generated in the brain is observed on an observing surface that is close to the surface of the brain, as shown in FIG. 2.

A virtual curved surface in the brain is considered, and current distribution on the virtual curved surface that recovers the observed magnetic field is calculated. When the virtual curved surface is moved to the inner side of the brain with the radius made gradually smaller, the expansion of the current distribution recovering the observed magnetic becomes smaller, and it becomes the smallest when the virtual surface encompasses the true current source. When the virtual curved surface is further moved to be deeper than the current source, the expansion of current distribution comes to be wider again, and the difference between the magnetic field generated by the current and the observed magnetic field also becomes larger.

Accordingly, the depth of the current source can be identified by reviewing the expansion of the current distribution recovering the observed magnetic field and the error in recovery of the magnetic field. Further, by calculating the current distribution on the virtual curved surface at the depth identified in this manner, the expansion of the current source can also be found. The foregoing is the principle of the present invention.

(Identification of Current Source Depth by Bayesian Estimation)

In order to specifically implement the principle of current source estimation described above, in the present invention, a procedure based on the following probability theory is employed. The procedure will be summarized in the following.

What can be observed by MEG or EEG is several to several hundreds of magnetic fields (electric fields) existing near the surface of the brain. In order to approximate the current distribution on the virtual curved surface, lattice points are set on the virtual curved surface, and a current dipole (or an appropriate current source model) is allocated to each lattice point. In order to estimate the current distribution with high resolution, it is necessary to increase the number of lattice points to increase the density of the lattice points.

When the number of lattice points on the virtual curved surface is increased to be larger than the number of observation points, a unique solution cannot be determined. When estimation points is larger in number than the observation points, the number of parameters to be estimated becomes larger than the number of observed data, and hence, the observed magnetic field would be better recovered even on a virtual surface that is positioned deeper than the current source.

In order to cope with such problems, the current distribution on the virtual curved surface is estimated utilizing Bayesian estimation theory. At the time of Bayesian estimation, prior distribution that represents prior information of the current source is used. Specifically, as it is considered that brain current sources exist localized at a plurality of positions, a prior distribution that leads to the smallest possible expansion of current distribution is introduced. Namely, a prior distribution is introduced in which a current dipole on a lattice point of which magnitude cannot be well identified only from the observed data comes to have a magnitude close to zero. This can be realized by introducing hierarchical prior distribution referred to as "Automatic Relevance Determination" prior distribution (Reference: R. M. Neal, Bayesian Learning for Neural Networks, Springer Verlag, 1996). This prior distribution will be hereinafter referred to as "localized condition prior distribution." The manner how to select a prior distribution introducing prior information other than the localized condition will be described later with reference to the second embodiment.

It is impossible, however, to analytically calculate posterior probability distribution from the localized condition prior distribution and observed data. Therefore, in the present invention, variational Bayes method is used as will be described later (Reference: H. Attias, Proc. 15th Conference on Uncertainty in Artificial Intelligence pp. 21-30, 1999 and Masa-aki Sato, Neural Computation, 13, 1649-1681, 2001). It is noted that other method of approximation such as Monte Carlo method may be used.

By Bayesian estimation using localized condition prior distribution, it becomes possible to obtain a current distribution on the virtual curved surface that recovers the observed data and has smallest possible expansion. Further, by comparing model posterior probabilities when estimations are made using virtual curved surfaces of different depths, the depth of the current source can be estimated.

The logarithm of the model posterior probability can be represented as a sum of log-likelihood term and model complexity term. The log-likelihood term becomes larger as recovery error becomes smaller.

The model complexity term becomes larger when the number of effective current dipoles (that is, having a magnitude not smaller than an appropriate threshold) on the lattice points becomes smaller. As already described, the recovery error and the expansion of the current distribution on the virtual curved surface (number of effective current dipoles) become the smallest when the depth of the virtual curved surface matches the current source. Thus, it can be understood that the model posterior probability becomes the largest at this time. In other words, the current source exists on the virtual curved surface at a depth at which the model posterior probability becomes the largest.

In summary, the present invention provides a method of estimating the position of the brain current source, depth direction inclusive, from the observed data of MEG and EEG.

The basic idea of the present invention comes from the fact that an electromagnetic field generated by a current source can be recovered by causing an appropriate current flow over a curved surface existing between the current source and an observing surface, and that the expansion of current distribution on the curved surface becomes smaller as the curved surface comes closer to the current source, as described above. The present invention is characterized in that, base on this idea, the position of the current source including the depth direction is estimated by considering the fact that the model posterior probability becomes the largest when the curved surface encompasses the current source in Bayesian estimation of the current distribution on the curved surface that recovers the observed data, that is, by considering the model posterior probability.

(Where There are Plurality of Current Sources)

Though description has been made on one current source, the method is also applicable even when there are a plurality of current sources.

The electromagnetic field generated by a current attenuates in inverse proportion to the square of distance, and therefore, the current source closest to the brain surface has the largest influence on the observed magnetic field on the brain surface. Therefore, it is possible to identify the current sources one by one in order, starting from the one closest to the brain surface.

When the virtual curved surface is moved deeper from the brain surface, the model posterior probability attains the relative maximum near a current source closest to the brain surface (which will be referred to as the first current source). When there are two or more current sources, there will be a plurality of local sets of current dipoles corresponding in number to the current sources, in the current distribution on the virtual curved surface.

The local set of current dipoles is referred to as localized current distribution. A local surface including individual localized current distribution is separated and moved in the depth direction to find the model posterior probability. When the local surface that corresponds to the first current source is moved, the model posterior probability attains to the relative maximum at the depth of the first current source. When other local surfaces are moved, the model posterior probability never attains to the relative maximum at the depth of the first current. Thus, the position of the first current source, that is, the position of the current source closest to the brain surface can be identified.

In order to find the second deepest current source, the local surface corresponding to the first current source is fixed, the depth of the remaining local surfaces are aligned and gradually made deeper. Then the model posterior probability attains the relative maximum at the second deepest current source. When the individual local surface is moved in the depth direction again, the model posterior probability attains to the relative maximum at the depth of the second current source, only when the local surface corresponding to the second current source is moved. In this manner, the position of the second current source can be identified. The third and the following current sources can also be identified in the similar manner.

The method is advantageous over the method in which the depth of individual local surface is moved independently, in that the time for computation can significantly be reduced.

(Method in Which Resolution is Increased Gradually)

According to the method of estimating brain current source of the present invention, it is possible to identify position of each of the current sources starting from the one closest to the brain surface in the above described manner and, in addition, it is possible to gradually increase the resolution of current source estimation.

First, a position of a current source is roughly estimated with a low resolution (with a small number of lattice points on the virtual curved surface and a small number of sample points in the depth direction). In this stage, the position of a local surface corresponding to each current source is approximately determined.

Next, estimation is made with higher resolution. At this time, the area of the local surface has become smaller as compared with the original virtual curved surface, and hence the resolution is naturally higher when the same number of lattice points are used. Accuracy in estimating the current source position can be improved by increasing the resolution in the depth direction as well. If the current distribution is further localized when the resolution is made higher, it is possible to estimate again with local surface made smaller and the resolution made still higher.

On the contrary, if the expansion of current distribution does not much vary even when the resolution is improved, it means that the current source expands wide. In this manner, the resolution can be adjusted in accordance with how the current source expands.

[Specific Procedure of Current Source Estimation]

In the following, specific procedure for identifying the position of a "brain current source" will be described in detail, in accordance with the outline above.

[(I) Preparation for Current Source Estimation]

First, preparation for the process procedure for estimating the current source will be described.

Specifically, for the estimation of current source, the following procedures must be taken in advance.

(I-1) Determination of the Shape of Virtual Curved Surface and Current Model (I-2) Further, in order to estimate the virtual current distribution while moving the virtual curved surface, it is necessary to determine sample points on the virtual curved surface and sample points in the depth direction.

(I-3) Further, as will be described in detail later, it is necessary to determine in advance meta parameters to designate the distribution shape of hierarchical prior distribution for estimating current distribution as initial values.

In the following, the procedure of (I-1) Determination of the shape of virtual curved surface and current model will be described in grater detail.

(I-1-1) Determination of the Shape of Virtual Curved Surface

The simplest shape of the virtual curved surface is obtained by regarding the brain as a hemisphere and assuming various hemispheres of different radii to be the virtual curved surfaces.

When a location where existence of a brain current is highly likely such as the cerebral cortex has been known in advance by other measuring method such as Magnetic Resonance Imaging: MRI, the shape of the virtual curved surface may be determined based on such information.

Particularly when the shape of the cerebral cortex is known with high precision and it is considered that the brain current source is non-existent in other regions, the current distribution estimation of cerebral cortex points may be performed while omitting the search in the depth direction, which will be described later. Further, it is also possible to perform the search in the depth direction only in a limited region.

In this case, the shapes of virtual curved surfaces having different depths may generally differ. It is necessary, however, to determine the shapes not to intersect with each other.

(I-1-2) Determination of Current Model

As a current model on the virtual curved surface, let us consider a current dipole model. It is also possible to consider other current models.

Consider appropriate lattice points (sample points) $\{X_n | n=1, \ldots, N\}$ on the virtual curved surface. Assume a current dipole of which current intensity is $j_n$ on each lattice point. Here, the magnetic field formed by the current dipole $j_n$ at a lattice point $X_n$ on an observation point $Y_i$ ($i=1, \ldots, I$) on the brain surface is given by the following Biot-Savart's expression.

$$\mu \frac{j_n \times (Y_i - X_n)}{|Y_i - X_n|^3}$$

Here, $\mu$ represents magnetic permeability, and by way of example, for a vector $X_n$, the expression $|X_n|$ represents the absolute value of vector $X_n$. As more accurate expression, Sarvas's expression with the brain regarded as a sphere filled with conductive solution (Reference: J. Sarvas, Phys. Med. Biol. 32, 11-22, 1987) may be used, or numerical solution such as given by finite element method or boundary element method may be used, considering detailed structure of the brain. In the following, Biot-Savart's expression above will be used, for simplicity of description and representation.

Here, the magnetic field formed by the current dipole $\{j_n | n=1, \ldots, N\}$ on an observation point $Y_i$ ($i=1, \ldots, I$) is represented by the following equation.

$$B(Y_i) = \sum_{n=1}^{N} \mu \frac{j_n \times (Y_i - X_n)}{|Y_i - X_n|^3}$$

Assuming that the direction of the magnetic field observed at the observation point $Y_i$ is a vector $S_{i,c}$ ($c=1, \ldots, C$), component $B_{i,c}$ in the direction of vector $S_{i,c}$ of the magnetic field at this point can be given as $$B_{i,c} = \sum_{n=1}^{N} \mu \frac{(j_n \times (Y_i - X_n)) \cdot S_{i,c}}{|Y_i - X_n|^3}$$

Further, when a local gradient of a magnetic field is to be measured as a magnetic field to be observed, a differentiation of the equation above by $Y_i$ will be observed.

When the direction of a current dipole at a lattice point $X_n$ (position vector) is restricted, the current dipole can be represented by the following equation, with a possible independent direction of the current dipole being $b_{n,d}$ ($d=1, \ldots, D$). In this equation, a case where D=3 corresponds to a case where there is no restriction on the direction.

$$j_n = \sum_{d=1}^{D} j_{n,d} \cdot b_{n,d}$$

In summary, a magnetic field formed by the current dipole at a lattice point $\{X_n | n=1, \ldots, N\}$ of the virtual curved surface on the observation point $Y_i$ can be given as $$B_{i,c} = \sum_{n=1}^{N} \sum_{d=1}^{D} j_{n,d} \cdot G(i, c; n, d)$$

$$G(i, c; n, d) = \mu \frac{(b_{n,d} \times (Y_i - X_n)) \cdot S_{i,c}}{|Y_i - X_n|^3}$$

Here, $j_{n,d}$ is an independent component of the current dipole at the lattice point $X_n$. Further, the function G (i, c; n, d) represents the component in $S_{i,c}$ direction of the magnetic field formed by the current dipole $j_{n,d}$ at the lattice point $X_n$.

The problem of estimating current distribution may be considered as a problem of estimating a current distribution on the virtual curved surface $\{j_{n,d} | n=1, \ldots, N; d=1, \ldots, D\}$ from the observed magnetic field $\{B_{i,c} | i=1, \ldots, I; c=1, \ldots, C\}$.

The measured value of the magnetic field at the observation point described above may be given by the following matrix expression. Here, G is referred to as a lead field matrix. When Sarvas's expression or a numerical solution such as obtained by the boundary element method is used in place of Biot-Savart's expression, the lead field matrix will have different values, and other portions of the following description are similarly applicable.

$$B = G \cdot J$$

$B = (B_{i,c} | i=1, \ldots, I; c=1, \ldots, C)$:(I×C) dimensional vector $J = (J_{n,d} | n=1, \ldots, N; d=1, \ldots, D)$:(N×D) dimensional vector $G = (G(i,c; n,d) | i=1, \ldots, I; c=1, \ldots, C; n=1, \ldots, N; d=1, \ldots, D)$:(I×C)×(N×D) dimensional matrix (Current Source Probability Model)

With the current model determined in this manner, the following "current source probability model" is introduced for such current distribution estimation.

(I-1-3) Current Source Probability Model

A probability model for the current model on the virtual curved surface described above will be considered.

It is assumed that the observed magnetic field is represented as a sum of the magnetic field formed by the current distribution J on the virtual curved surface and the observation noise. Further, it is assumed that the observation noise is Gaussian noise having an independent variance $\sigma^2$ at each measuring point.

More generally, it may be possible to consider Gaussian noise having a multidimensional normal distribution, in which correlation between noises at respective measuring points is represented in the form of a covariance matrix. For simplicity of description, an isotropic homoscedastic noise model will be employed in the following.

Specifically, the observed magnetic field is considered as $$B = G \cdot J + \xi$$

$J = J_{virtual\ curved\ surface} = (j_{n,d} | n=1, \ldots, N; d=1, \ldots, D)$ $G = (G(i,c;n,d) | i=1, \ldots, I; c=1, \ldots, C; n=1, \ldots, N; d=1, \ldots, D)$ $\xi = (\xi_{i,c} | i=1, \ldots, I; c=1, \ldots, C)$ :Gaussian Noise with each Component Having Independent Variance $\sigma^2$ The probability distribution for the current model may be considered as follows.

First, a virtual surface at a specific depth, or a set of local surfaces with the depth of each local surface identified, will be represented by M. When a current distribution J on the virtual curved surface M is given, the probability P(B|J, β, M) that the observed magnetic field is B is represented by the following equation, where $\beta = 1/\sigma^2$.

$$P(B | J, \beta, M) = \exp\left[-\frac{1}{2}\beta|B - G \cdot J|^2 + \frac{1}{2}(I \cdot C)\log(\beta/2\pi)\right]$$

$$\beta = 1/\sigma^2$$

(I-1-4) Hierarchical Prior Distribution

As already described, localized condition hierarchical prior distribution will be used as the prior distribution for the current distribution J on the virtual curved surface M.

The prior distribution for the current distribution J before observation (probability of J being realized) is represented by the following equation, under the assumption of localized condition hierarchical prior distribution.

$$P_0(J\mid\alpha,\beta,M)=\exp\left[-\frac{1}{2}\beta\sum_{n=1}^{N}\alpha_n\left(\sum_{d=1}^{D}j_{n,d}\right)^2+\frac{D}{2}\sum_{n=1}^{N}\log(\beta\alpha_n/2\pi)\right]$$

$$P_0(\beta\mid\tau,M)=\Gamma(\beta\mid 1/\tau,\gamma_{\beta 0})$$

Here, Γ( . . . ) represents gamma distribution, which is defined below. In the expression below, Γ($\gamma_0$) is a gamma function, which is also defined below.

$$\Gamma(\beta\mid b,\gamma_0)\equiv\frac{1}{\beta}(\gamma_0\beta/b)^{\gamma_0}\frac{1}{\Gamma(\gamma_0)}e^{-\gamma_0\beta/b}$$

$$\Gamma(\gamma_0)\equiv\int_0^\infty dt\, t^{\gamma_0-1}e^{-t}$$

Further, α and τ are hyper parameters introduced to model the current distribution J and prior distribution for inverse variance of noise β. Hierarchical prior distributions $P_0(\alpha\mid M)$ and $P_0(\tau\mid M)$ for α and τ are $$P_0(\alpha\mid M)=\prod_{n=1}^{N}\Gamma(\alpha_n\mid\bar{\alpha}_0,\gamma_{\alpha 0})$$

$$P_0(\tau\mid M)=\Gamma(\tau\mid\bar{\tau}_0,\gamma_{\tau 0})$$

In the equations above, meta parameters bar $\alpha_0$, $\gamma_{\alpha 0}$, $\tau_0$ and bar $\gamma_{\tau 0}$ determining the distribution shape of the hierarchical prior distributions $P_0(\alpha\mid M)$ and $P_0(\tau\mid M)$ for α and τ will be described in detail later. Here, "bar" preceding a name of a variable means that the variable has the sign "-" thereabove.

(I-1-5) Bayesian Estimation

When data B of a magnetic field is observed, the posterior probability distribution P(J|B, M) that the current distribution is J can be calculated in the following manner, using Bayesian theorem.

$$P(J\mid B,M)=\int d\beta\, d\alpha\, d\tau\, P(J,\beta,\alpha,\tau\mid B,M)$$

Here, the posterior probability distribution P(J, β, α, τ|B, M) is given as $$P(J,\beta,\alpha,\tau\mid B,M)=$$

$$\frac{P(B\mid J,\beta,M)P_0(J\mid\alpha,\beta,M)P_0(\beta\mid\tau,M)P_0(\alpha\mid M)P_0(\tau\mid M)}{P(B\mid M)}$$

$$P(B\mid M)=\int dJ\, d\beta\, d\alpha\, d\tau\, P(B\mid J,\beta,M)$$

$$P_0(J\mid\alpha,\beta,M)P_0(\beta\mid\tau,M)P_0(\alpha\mid M)P_0(\tau\mid M)$$

Using this posterior distribution, an expected value E[J|B, M] is given as $$\bar{J}=E[J\mid B,M]=\int dJ\, d\beta\, d\alpha\, d\tau\, P(J,\beta,\alpha,\tau\mid J,M)J$$

Further, P(B|M) represents marginal likelihood of the virtual curved surface model M. When the depth of a current source is estimated, a number of models having different depths are compared. At this time, it is assumed that there is no prior information about the depth. Specifically, in the following, it is assumed that P(M)=constant.

When the observation data B is given, the probability that the model M is a true model, that is, the model posterior probability P(M|B), is in proportion to the model marginal likelihood P(B|M) under the assumption described above, and hence, the following relation holds.

$$P(M\mid B)\propto P(B\mid M)$$

(I-1-6) Variational Bayes Method

It is generally impossible to analytically calculate the model marginal likelihood when the probability model and the hierarchical prior distribution are given.

Therefore, as a method of calculating by approximation the model marginal likelihood, variational Bayes method is used. It is possible to use other method of approximation, such as Monte Carlo method and Laplacian approximation.

The "variational Bayes method" will be briefly outlined, and specific procedure will be described later.

In order to calculate a true posterior distribution P(J, β, α, τ|B, M) by approximation, a trial posterior distribution Q(J, β, α, τ) is considered.

Closeness between the two probability distributions P(J, β, α, τ|B, M) and Q(J, β, α, τ) can be calculated by using K-L distance given by the following expressions.

$$KL(Q\|P)=\int dJ\, d\beta\, d\alpha\, d\tau\, Q(J,\beta,\alpha,\tau)\log\left[\frac{Q(J,\beta,\alpha,\tau)}{P(J,\beta,\alpha,\tau\mid B,M)}\right]$$

$$=\log P(B\mid M)-F(Q)\geq 0$$

$$F(Q)\equiv\int dJ\, d\beta\, d\alpha\, d\tau\, Q(J,\beta,\alpha,\tau)\times$$

$$\log\left[\frac{P(B\mid J,\beta,M)P_0(J\mid\alpha,\beta,M)P_0(\beta\mid\tau,M)P_0(\alpha\mid M)P_0(\tau\mid M)}{Q(J,\beta,\alpha,\tau)}\right]$$

The K-L distance attains to zero only when the two distributions are equal to each other, and otherwise it always assumes a positive value.

When a free energy F(Q) for the trial posterior distribution Q is defined in the expression above, the following inequality results.

$$F(Q)\leq\log P(B\mid M)$$

Specifically, the distribution Q(J, β, α, τ) that maximizes the free energy F(Q) becomes equal to the true posterior distribution P(J, β, α, τ|B, M), and at this time, the free energy is equal to the marginal log-likelihood.

According to variational Bayes method, the form of function Q(J, β, α, τ) is restricted to the following form, to maximize the free energy.

$$Q(J,\beta,\alpha,\tau)=Q_J(J,\beta)Q_\alpha(\alpha,\tau)$$

By alternately repeating the step of fixing the second term Qα on the right side of the equation above and maximizing F(Q) with respect to the first term $Q_J$ on the right side and the step of fixing the first term $Q_J$ and maximizing F(Q) with respect to the second term Qα, a distribution Q* is obtained that attains the relative maximum of free energy F(Q).

[(II) Procedure of Current Source Estimation]

A specific procedure for estimating the current source after the preparation above will be described with reference to the figures.

Figure 4:
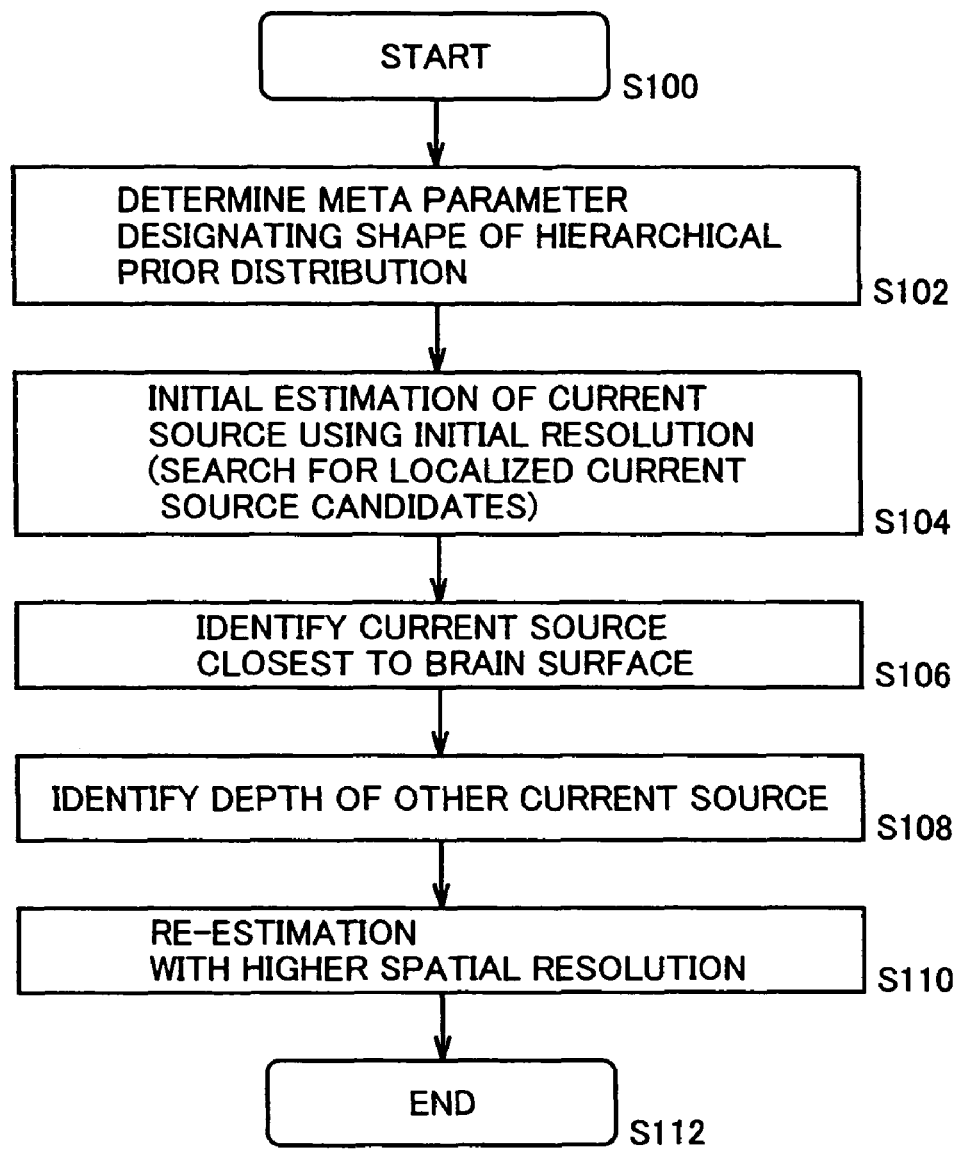
FIG. 4 is a flow chart representing an overall procedure of the brain current source estimating method in accordance with the present invention.

FIG. 4 is a flow chart representing an overall procedure of the brain current source estimating method in accordance with the present invention.

Referring to FIG. 4, first, when the process of estimating a position of a brain current source starts (step S100), values of meta parameters for designating the shape of hierarchical prior distribution for estimating the current distribution and an initial value of a variable to be estimated are determined (step S102).

Thereafter, initial estimation of the current source is performed, using an initial resolution, so as to extract candidates of the current source (step S104).

Then, among the current source candidates extracted in this manner, a position of a current source that is closest to the brain surface is estimated (step S106). Thereafter, depths of other current sources is identified successively (step S108).

After the positions of current sources are identified with the first resolution in the above described manner, re-estimation of the positions of the current sources is performed with the spatial resolution increased (step S110), and the process ends (step S112).

Processes of respective steps of FIG. 4 will be described in grater detail in the following.

(II-1) Initial Estimation of Current Source Using Initial Resolution (Extraction of Current Source Candidates)

Figure 5:
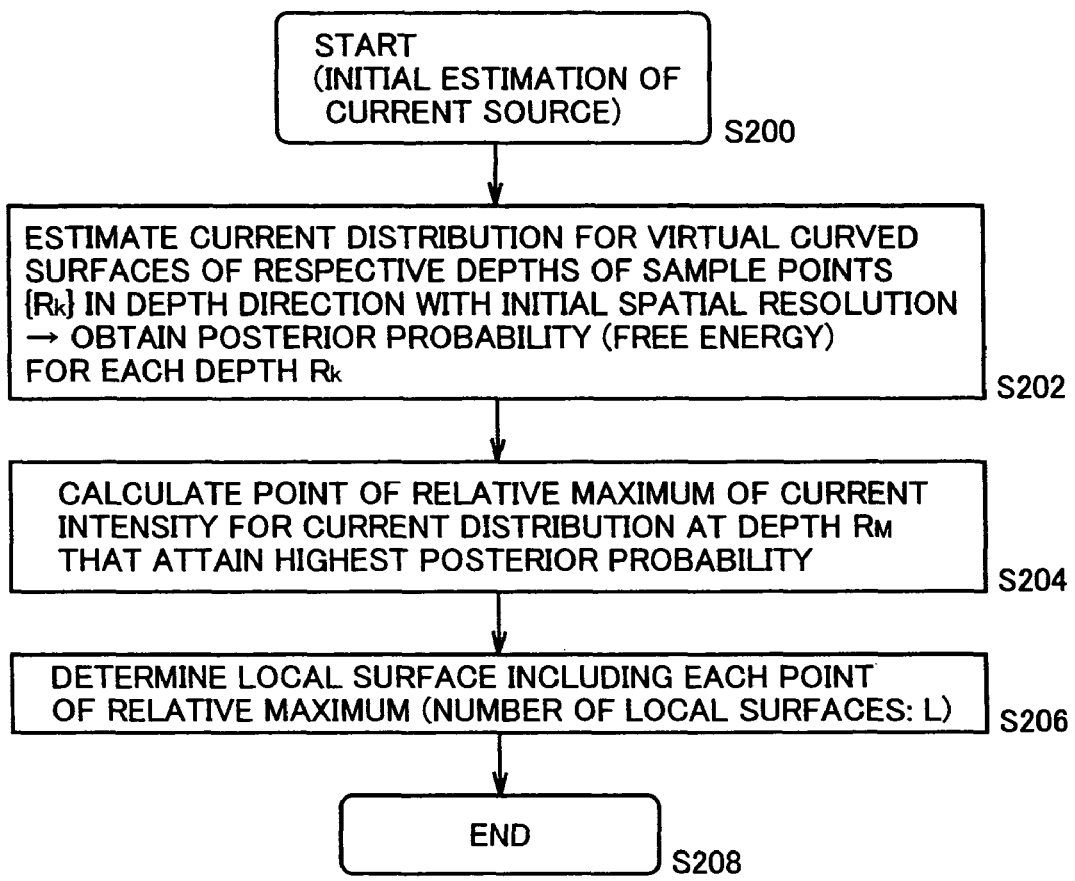
FIG. 5 is a flow chart representing a process of initial estimation of the current source using an initial resolution.

FIG. 5 is a flow chart representing the process of step S104 among the steps shown in FIG. 4, that is, the process of initial estimation of the current source using an initial resolution.

Referring to FIG. 5, first, sample points in the depth direction with the initial resolution are determined to be $\{Rk|k=1, \ldots, K\}$. Current distribution is estimated for the virtual curved surface at each depth $Rk$. Further, based on the current distribution estimated in this manner, posterior probability for each depth $Rk$ is calculated. The posterior probability corresponds to the free energy value, which will be described later (step S202).

For the current distribution at the depth $R_M$ at which the posterior probability calculated in this manner becomes the highest, a relative maximum point of current intensity is found (step S204).

Further, a local surface that encompasses each relative maximum point is determined. Assuming that there are L local surfaces, each local surface will be the candidate of localized current source (step S206).

In the following, the process of step S102 of FIG. 4 and the process of step S202 of FIG. 5 that follows, will be described in grater detail.

(II-1-1) Determination of Meta Parameter Values for Designating Shape of Hierarchical Prior Distribution for Estimating Current Distribution and Initial Values of Variables to be Estimated As described above, estimation of a current source is performed using variational Bayes method. Therefore, the process of step S102 shown in FIG. 4 is performed in the following manner, with the application of variational Bayes method.

By way of example, the meta parameters designating the shape of hierarchical prior distribution are determined as follows.

$\gamma_{\beta 0} = 1$ (more generally, $0 \leq \gamma_{\beta 0}$)

$\gamma_{\tau 0} = 0$ (more generally, $0 \leq \gamma_{\tau 0}$)

$\gamma_{\alpha 0} = 0.1$ (more generally, $0 \leq \gamma_{\alpha 0}$)

$\overline{\tau}_0 = \kappa_\tau \cdot V_{ar}(B), \kappa_\tau = 1$ (more generally, $\kappa_\tau \sim 1$)

$V_{ar}(B) = \frac{1}{I \cdot C} \sum_{i=1}^{I} \sum_{c=1}^{C} (B_{i,c} - \overline{B})^2$ $\overline{B} = \frac{1}{I \cdot C} \sum_{i=1}^{I} \sum_{c=1}^{C} B_{i,c}$ $\overline{\alpha}_o = \kappa_\alpha \cdot \frac{1}{\tilde{N}} Tr(G' \cdot G), \kappa = 10$ (more generally, $0 < \kappa_\alpha$)

$\tilde{N} = D \cdot N$

Further, based on the equations above, each variable is initialized in the following manner.

$\gamma_\beta = \frac{1}{2} I \cdot C + \gamma_{\beta 0}$ $\gamma_\tau = \gamma_{\tau 0} + \gamma_{\beta 0}$ $\gamma_\alpha = \gamma_{\alpha 0} + \frac{1}{2} D$ $\overline{\alpha}_n = \overline{\alpha}_0$ $\overline{\tau} = \overline{\tau}_0$ $\sum_G = G' \cdot G$ (II-1-2) Specific Process of Variational Bayes Method for Estimating Current Distribution (1) Calculation of Expected Values of Parameters J, β (J-Step Process)

Here, expected values of parameters J and β are calculated. By this process, the free energy F(Q) for $Q_J$ is maximized.

By defining a diagonal matrix A as follows, $Q_J$ is derived in accordance with the following equations. In the following equations, an expected value of a variable is represented by the variable name with "-" attached thereabove.

$\overline{A}(n, d; n', d') = \delta_{nn'} \delta_{dd'} \overline{\alpha}_n \ (n, n' = 1, \ldots, N; d, d' = 1, \ldots, D)$ $\sum = \sum_G + \overline{A}$ $\overline{J} = \sum^{-1} \cdot G' \cdot B$ $\overline{\beta} = \gamma_\beta \left[ \frac{1}{2} |B - G \cdot \overline{J}|^2 + \frac{1}{2} \overline{J}' \overline{A} \overline{J} + \gamma_{\beta 0} \overline{\tau} \right]^{-1}$ $Q_J(J, \beta) = Q_J(J | \beta) Q_\beta(\beta)$ $Q_J(J | \beta) = \exp\left[-\frac{1}{2} \beta (J - \overline{J})' \sum (J - \overline{J}) + \frac{1}{2} \log\left|\sum\right| + \frac{1}{2} \tilde{N} \log(\beta / 2\pi)\right]$ $Q_\beta(\beta) = \Gamma(\beta | \overline{\beta}, \gamma_\beta)$ (2) Calculation of Expected Values of Hyper Parameters, that is, Calculation of Expected Values of Parameters α, τ (Process for α-Step)

Following the J step, expected values of hyper parameters α and τ are calculated. In this step, a process is performed to maximize the free energy F(Q) for $Q_\alpha$.

The procedure can be represented as $\overline{\alpha}_n = \gamma_\alpha \left[ \gamma_{\alpha 0} \overline{\alpha}_0^{-1} + \frac{1}{2} \overline{\beta} \sum_{d=1}^{D} \overline{J}_{n,d}^2 + \sum_{d=1}^{D} (\sum^{-1})(n, d; n, d) \right]^{-1}$ $(n = 1, \ldots, N)$ $\overline{\tau} = \gamma_\tau [\gamma_{\tau 0} \overline{\tau}_0^{-1} + \gamma_{\beta 0} \overline{\beta}]^{-1}$ $Q_\alpha(\alpha, \tau) = \Gamma(\tau | \overline{\tau}, \gamma_\tau) \prod_{n=1}^{N} \Gamma(\alpha_n | \overline{\alpha}_n, \gamma_\alpha)$ (3) Calculation of Free Energy Using $Q_J$ and $Q_\alpha$ calculated through the J step and α step as described above, the free energy is calculated in the following manner.

$$F = LP + H_J + H_\beta + H_\alpha + H_\tau$$

$$LP = -\frac{1}{2}\overline{\beta}|B - G \cdot \overline{J}|^2 - \frac{1}{2}Tr\sum\nolimits^{-1}\sum\nolimits_G +$$

$$\frac{1}{2}(I \cdot C) \ (<\log\beta> - \log 2\pi)$$

$$<\log\beta> = \log\overline{\beta} + \psi(\gamma_\beta) - \log\gamma_\beta$$

$$\psi(\gamma) \equiv \frac{d(\log\Gamma(\gamma))}{d\gamma} \quad \psi:\text{digamma function}$$

$$H_J = -\frac{1}{2}\left[Tr\sum\nolimits^{-1}\overline{A} - \log\left|\sum\nolimits^{-1}\overline{A}\right| - \tilde{N}\right] - \frac{1}{2}\overline{\beta}\overline{J}'\overline{A}\overline{J}$$

$$H_\beta = \gamma_{\beta 0}[\log(\overline{\tau}\overline{\beta}) - \overline{\tau}\overline{\beta} + 1] + \Phi(\gamma_\beta, \gamma_{\beta 0})$$

$$\Phi(\gamma, \gamma_0) \equiv (\log\Gamma(\gamma) - \gamma\psi(\gamma) + \gamma) - (\log\Gamma(\gamma_0) - \gamma_0\log\gamma_0 + \gamma_0) +$$

$$\gamma_0(\psi(\gamma) - \log\gamma)$$

$$H_\tau = \gamma_{\tau 0}[\log(\overline{\tau}/\tau_0) - (\overline{\tau}/\tau_0) + 1]$$

$$H_\alpha = \sum_{n=1}^{N} \gamma_{\alpha 0}[\log(\overline{\alpha}_n/\overline{\alpha}_0) - (\overline{\alpha}_n/\overline{\alpha}_0) + 1]$$

In this manner, the process from the J step to calculation of free energy described above is repeated until the value of free energy F converges. The value of free energy F(Q) after convergence gives an approximation of marginal log-likelihood log P (B|M).

Further, model log-posterior probability differs only by the constant from log P (B|M), and therefore, the model having the maximum model posterior probability is the same as the model of which free energy is the highest, in accordance with the above described approximation.

By the above described procedure, posterior probability for the depth Rk can be calculated. By performing the processes of steps S204 and S206 of FIG. 5 accordingly, it is possible to find candidates of current sources localized to respective local surfaces.

(II-2) Identification of Current Source Closest to the Brain Surface

Next, the process of step S106 of FIG. 4, that is, the process for identifying the current source closest to the brain surface among the candidates of current sources found in the manner as described above, will be described.

Figure 6:
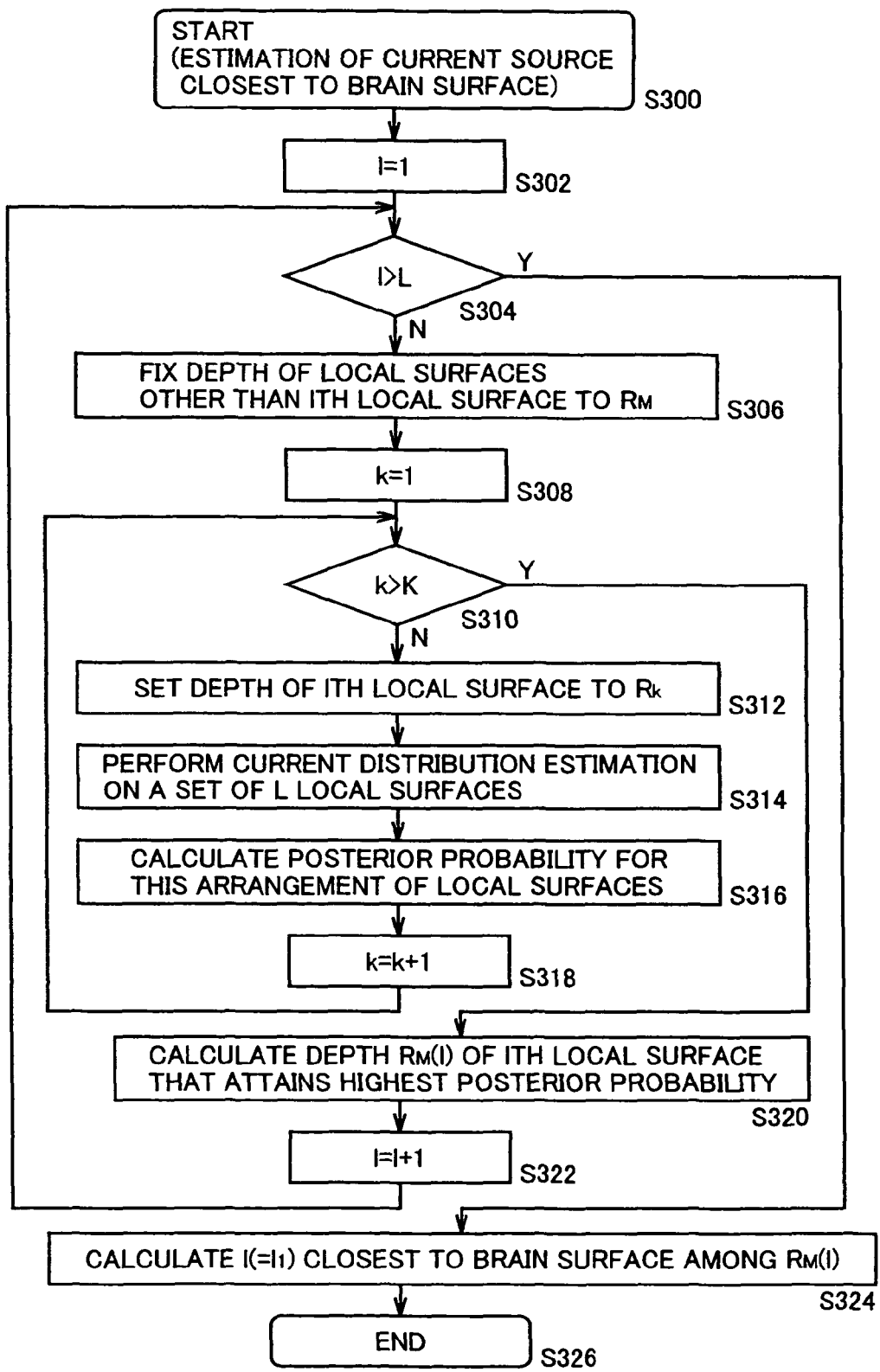
FIG. 6 is a flow chart representing a process for identifying a current source closest to the brain surface.

FIG. 6 is a flow chart representing a process for identifying a current source closest to the brain surface.

First, as the initial value, the value of a variable l is set to 1 (step S302). Then, the variable l is compared with a possible maximum value L of variable l (step S304), and when the variable l is not larger than the maximum value L, the process proceeds to step S306, and when the variable l exceeds the maximum value L, the process proceeds to step S324 (step S304). Specifically, the process from step S306 to step S322 is repeated from l=1 to l=L.

In step S306, depth of a local surface other than the lth local surface is fixed at the depth $R_M$ calculated in step S204 of FIG. 5.

The value of variable k is set to 1 (step S310). Thereafter, the variable k is compared with a possible maximum value K of variable k (step S310), and when the variable k is not larger than the maximum value K, the process proceeds to step S312, and when the variable k exceeds the maximum value K, the process proceeds to step S320.

In step S312, the depth of the lth local surface is first determined to be $R_k$.

Thereafter, current distribution is estimated for the set of L local surfaces (step S314).

Thereafter, the posterior probability (free energy) for this arrangement of the local surfaces is calculated (step S316). By incrementing the value of variable k by only 1 (step S318), the process returns to step S310.

The process is performed for each of the local surfaces having the depths from k=1 to k=K, and then, the depth $R_M(l)$ of the first local surface that provides the highest posterior probability is calculated (step S320). By incrementing the value of variable l only by 1 (step S322), the process returns to step S304.

In this manner, among the depths $R_M(l)$ calculated for each variable l, one closest to the brain surface (shallow) is detected, which is denoted by $l_1$ (step S324).

Through the steps described above, it follows that the $l_1$th local surface corresponds to the current source closest to the brain surface, the initial estimate value of the depth thereof is calculated as $R_M(l_1)$, and the process terminates (step S326).

Figure 7:
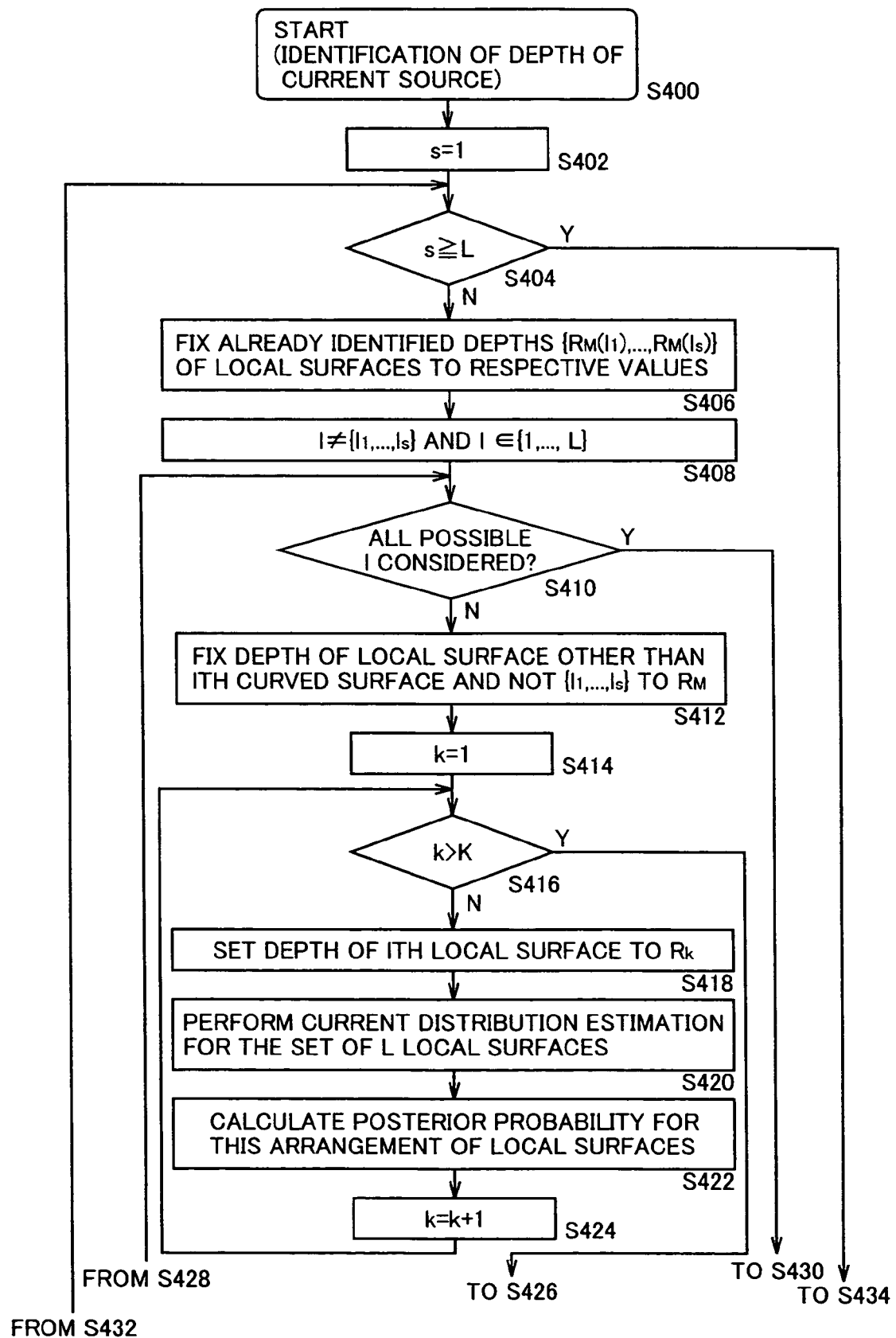
FIG. 7 is a first flow chart representing a process for identifying depth of a current source corresponding to each local surface.
Figure 8:
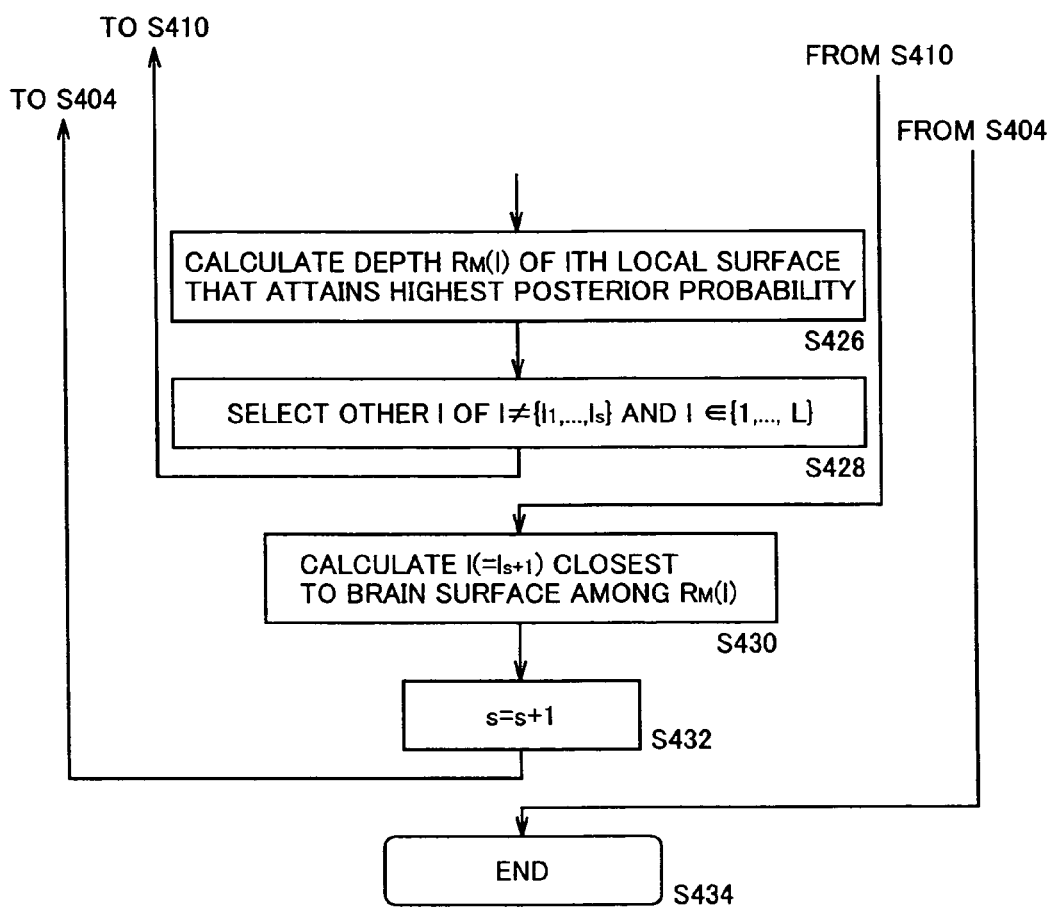
FIG. 8 is a second flow chart representing a process for identifying depth of a current source corresponding to each local surface.

(II-3) Identification of Depth of Current Source Corresponding to each Local Surface FIGS. 7 and 8 are flow charts representing a process for identifying depth of a current source corresponding to each local surface.

Referring to FIG. 7, the value of a variable s is set to 1 as an initial value (step S402). Thereafter, the variable s is compared with a possible maximum value L of variable s (step S404), and when the variable s is not larger than the maximum value L, the process proceeds to step S406, and when the variable s exceeds the maximum value L, the process proceeds to step S434 (step S404). Specifically, the process from step S406 to step S432 is repeated from s=1 to s=L.

In step S406, when the depths of local surfaces identified so far are represented as $\{R_m(l_1), \ldots, R_M(l_s)\}$, the depths of these local surfaces are fixed at $\{R_M(l_1), \ldots, R_M(l_s)\}$, respectively (step S406).

First, it is assumed that l is not equal to any of $\{l_1, \ldots, l_s\}$, and that l belongs to a set of $\{1, \ldots, L\}$ (step S408). Then, whether all possible values are considered as the value of variable l or not is determined (step S410), and if all the possible values have been considered, the process proceeds to step S430. Otherwise, the process proceeds to step S412.

In step S412, the depth of a local surface that is different from the lth local surface and not any of $\{l_1, \ldots, l_s\}$ is fixed at RM.

The value of variable k is set to 1 (step S414). Thereafter, the variable k is compared with a possible maximum value K of variable k (step S416), and when the variable k is not larger than the maximum value K, the process proceeds to step S418, and when the variable k exceeds the maximum value K, the process proceeds to step S426. Specifically, the process from step S418 to step S424 is repeated from k=1 to k=K.

In step S418, the depth of the first local surface is set to $R_k$.

Thereafter, for the set of L local surfaces, current distribution is estimated (step s420).

Further, posterior probability (free energy) for this arrangement of the local surfaces is calculated (step 422).

Referring to FIG. 8, in step S426, after the process to k=K is finished in the above described manner, the depth $R_M(l)$ of the lth local surface attaining the highest posterior probability is calculated (step S426).

Then, other variable l that is not equal to any of $\{l_1, \ldots, l_s\}$ belongs to the set of $\{1, \ldots, L\}$ and is not yet processed is selected (step S428), and the process returns to step S410.

Through the above described steps, among $R_M(l)$ values corresponding to all the processed variables l, the value l that is closest to the brain surface is calculated and denoted by $l_{s+1}$ (step S430).

Further, s is replaced by s+1 (step S432), and the process returns to step S404.

When the process ends for all the possible values s, identification of the depths of current sources corresponding to respective local surfaces is finished (step S434).

(II-4) Re-Estimation with Increased Resolution

Figure 9:
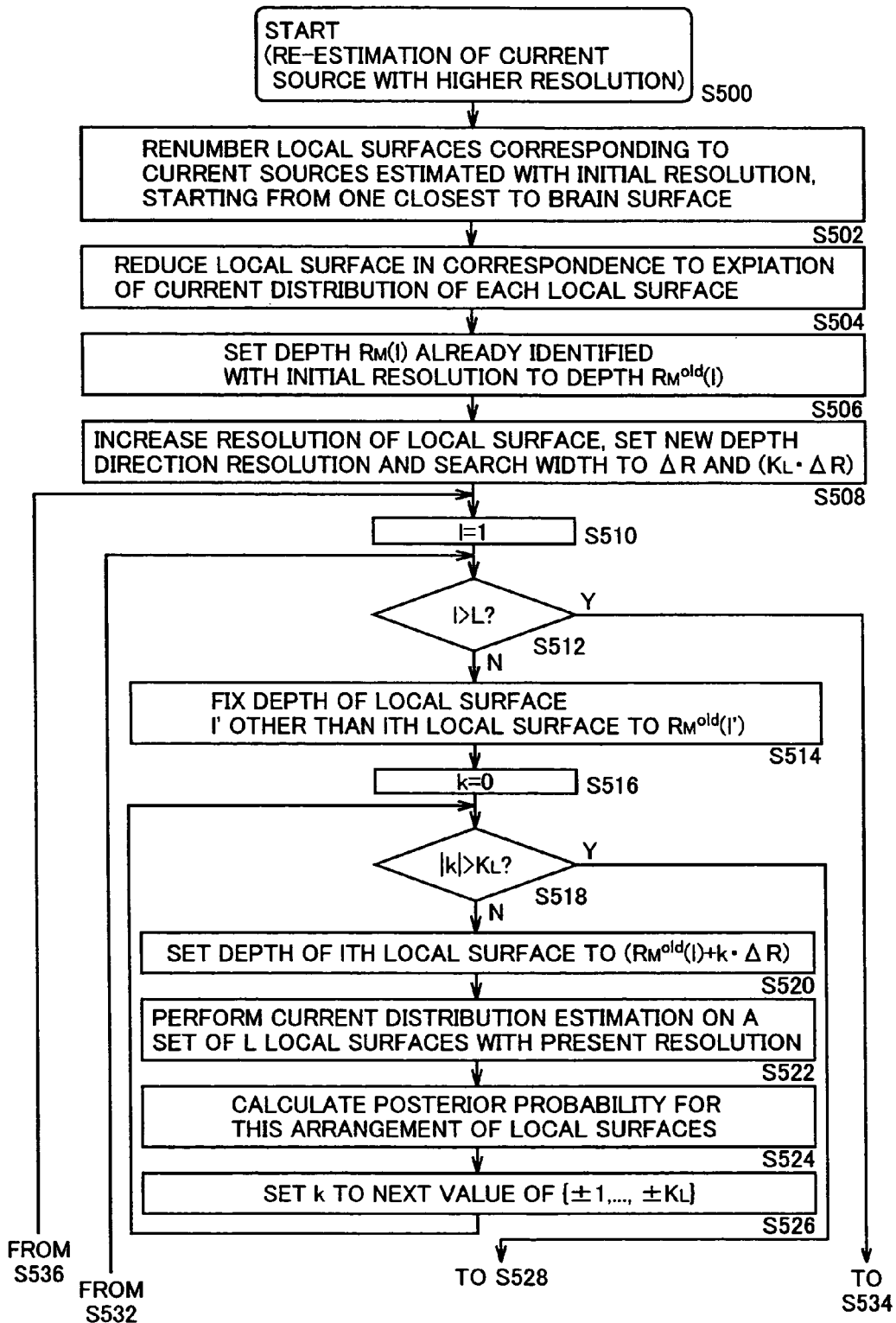
FIG. 9 is a first flow chart representing a process for re-estimating a position of a current source with higher spatial resolution.
Figure 10:
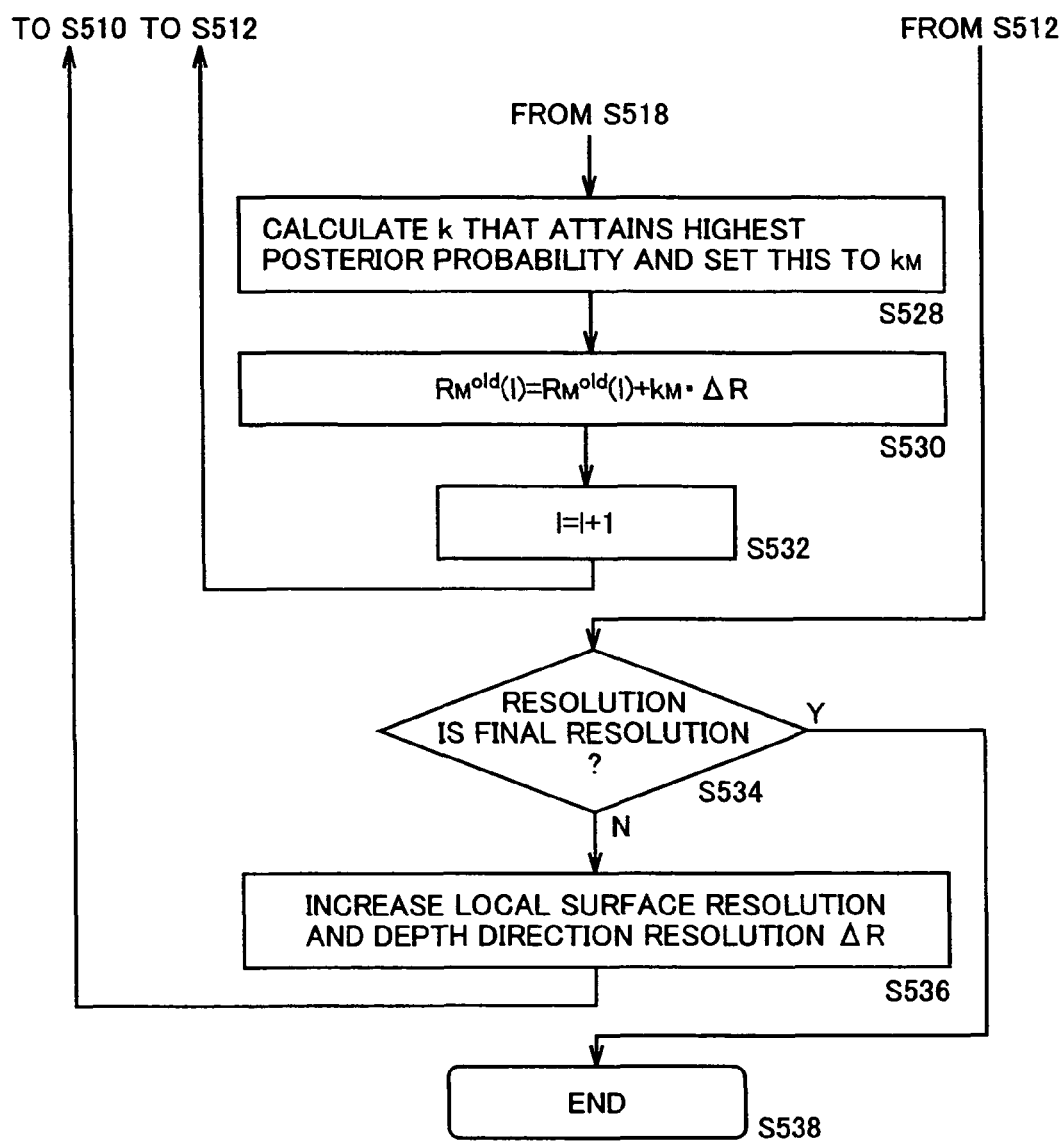
FIG. 10 is a second flow chart representing a process for re-estimating a position of a current source with higher spatial resolution.

FIGS. 9 and 10 are flow charts representing the process of step S110 shown in FIG. 4, that is, the process for re-estimating a position of a current source with higher spatial resolution.

Referring to FIGS. 9 and 10, first, numbers of local surfaces corresponding to the current sources estimated using the initial resolution are re-numbered so that the surfaces have the numbers 1, 2, 3, . . . , L starting from the one closest to the brain surface (step S502). Then, corresponding to the expansion of current distribution on each local surface, the local surface is made smaller (step S504).

The depth of the local surface $R_M(l)$ calculated by the process up to step S108 of FIG. 4 is denoted as $R_M^{old}(l)$ (step S506).

New resolution and search width in the depth direction are respectively represented as $\Delta R$ and $(K_L \cdot \Delta R)$. Further, resolution of lattice points on the local surface is also increased (step S508).

The value of a variable l is set to 1 as an initial value (step S510). Thereafter, the variable l is compared with a possible maximum value L of variable l (step S512), and when the variable l is not larger than the maximum value L, the process proceeds to step S514, and when the variable l exceeds the maximum value L, the process proceeds to step S534 (step S512). Specifically, the process from step S514 to step S532 is repeated from l=1 to l=L.

In step S514, the depth of a local surface l' other than the lth local surface is fixed to $R_M^{old}(l')$.

Further, the process from step S518 to step S526 is performed with k=0, ±1, . . . , ±$K_L$.

First, the value of variable k is set to 0 (step S516). Thereafter, the absolute value of variable k is compared with the possible maximum absolute value of $K_L$ (step S518), and when the absolute value of variable k is not larger than the maximum value $K_L$, the process proceeds to step S520, and when the absolute value of variable k exceeds the maximum value $K_L$, the process proceeds to step S528 (step S518).

In step S520, the depth of the lth local surface is set to $(R_M^{old}(l)+k \cdot \Delta R)$.

Thereafter, for the set of L local surfaces, current distribution is estimated using the present resolution (step S522).

Further, posterior probability (free energy) for this arrangement of the local surfaces is calculated (step S524). Then, the value k is set to the next one of $\{\pm 1, \ldots, \pm K_L\}$, and the process returns to step S518.

After the above described process is performed until k=±$K_L$, the value k that provides the highest posterior probability is calculated in step S528, which value is denoted by $k_{M'}$.

Then, $R_M^{old}(l)$ is replaced by $R_M^{old}(l)+k_{M'} \cdot \Delta R$ (step S530). The value of variable l is incremented by only 1 (step S532), and the process returns to step S512.

When the above described process has been performed until the value of variable l attains to the maximum value L and the resolution has reached the final resolution (step S534), the process is terminated (step S538).

When the resolution is not yet the final resolution (step S534), the resolution of the lattice points on the local surface and the resolution in the depth direction are increased (step S536), and the process returns to step S510.

By the "method of estimating brain current source" as described above, it becomes possible to estimate the position of a brain current source, including the position in the depth direction, from observation data of MEG (or EEG). Further, such estimation in the depth direction is applicable even when there are a plurality of current sources. Still further, the method is applicable when the current sources are localized as in the case of current dipoles or when the current source has an expansion. In addition, by the method, it is possible to estimate how the current source expands.

By additionally performing the process described with reference to FIGS. 9 and 10 after the estimation with the initial resolution, it becomes possible to successively increase resolution for estimating a position. This also means that it is possible to review with the scope of search restricted based on physiological findings or data obtained by other observation method.

[Result of Simulation]

In the following, simulation results will be described, in which current source positions of an assumed model were estimated in accordance with the method of estimating brain current source described above.

Figure 11:
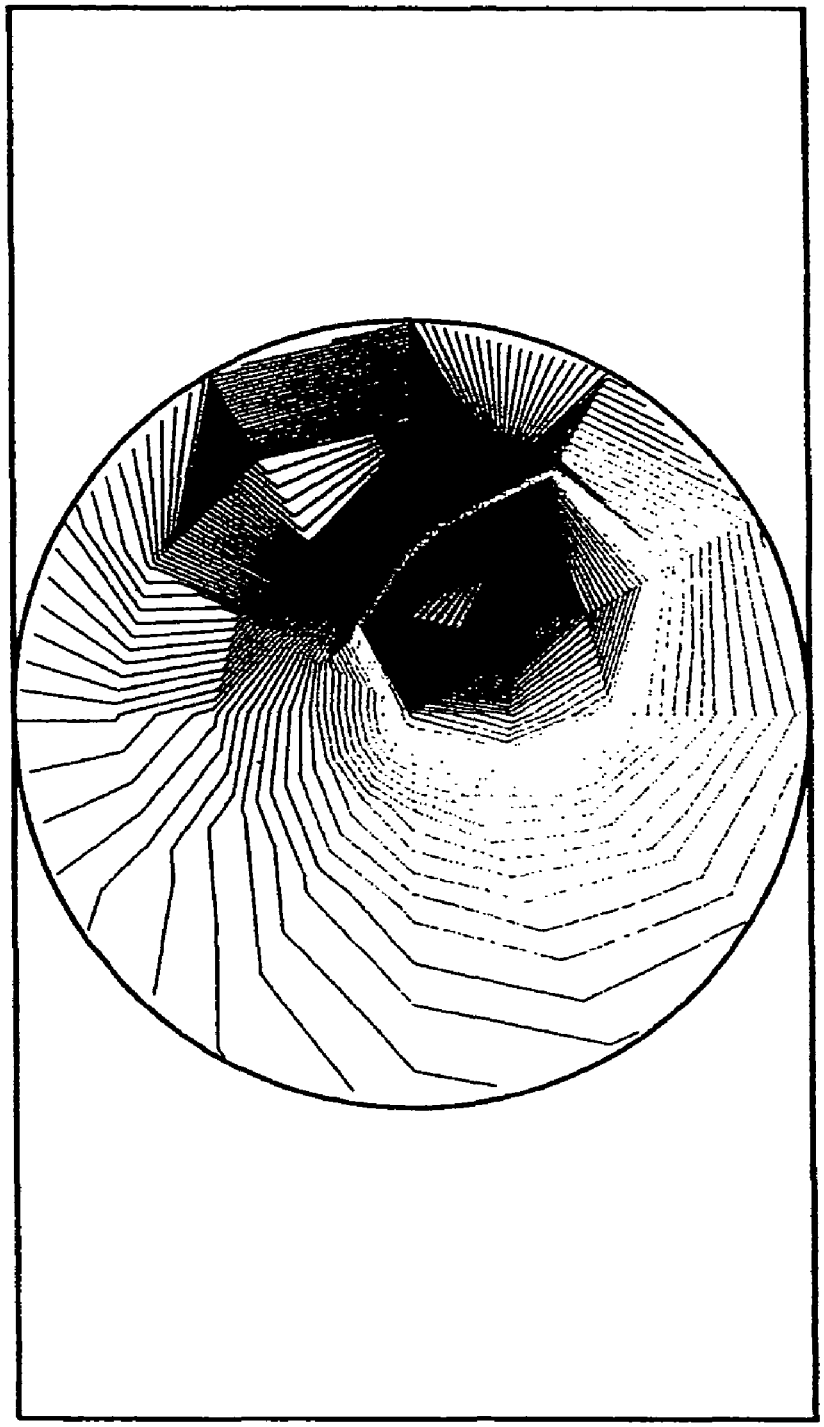
FIG. 11 is a top view of a magnetic field distribution observed on a surface of a hemisphere, assuming that the human brain is a hemisphere.

FIG. 11 is a top view of a magnetic field distribution in the radial direction observed on a surface of a hemisphere, assuming that the human brain is a hemisphere having the radius of 10.0 (arbitrary unit).

FIG. 11 shows a magnetic field distribution on a surface of the hemisphere in which a single current source is positioned at a radius of 7.0 from the center, as will be described later. In the simulation that will be discussed below, noise having the S/N ratio of 0.1 is added to the observation data of the magnetic field.

Figure 12A:
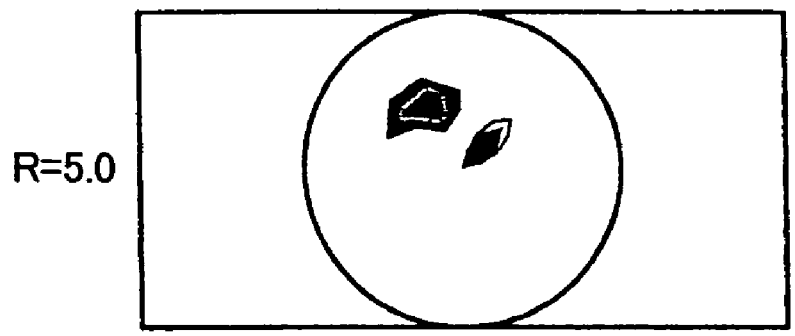
FIGS. 12(a), 12(b) and 12(c) represent results of initial estimation of current sources using initial resolution, where the radius is R=5.0, R=6.0 and R=7.0, respectively.
Figure 12B:
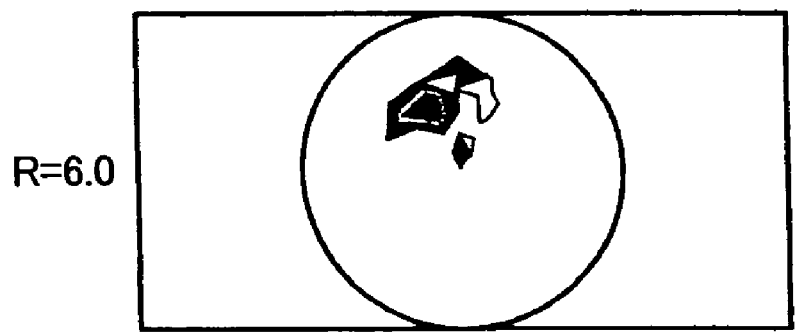
Figure 12C:
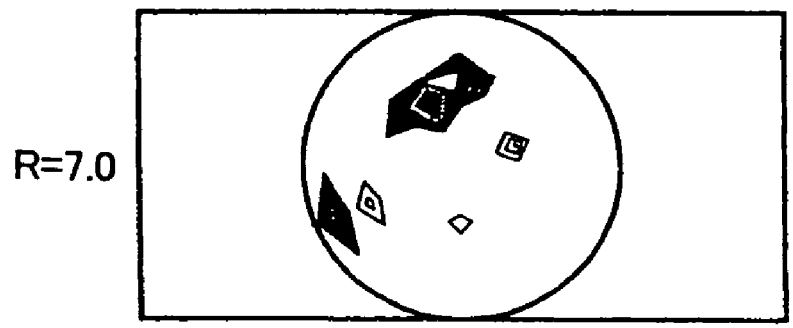

FIG. 12 represents results of initial estimation of current sources using initial resolution.

FIG. 12 shows the result of calculation of current distribution, in which, as described with reference to the process of steps S102 to S104 of FIG. 4, in order to perform initial estimation of the current source using the initial resolution, the depth (radius) is changed stepwise and on the hemisphere of each depth, the current distribution that attains the maximum free energy is calculated in accordance with variational Bayes method.

FIG. 12(a) shows the result where the radius is R=5.0, 12(b) shows the result where the radius is R=6.0 and 12(c) shows the result where the radius is R=7.0.

Figure 13D:
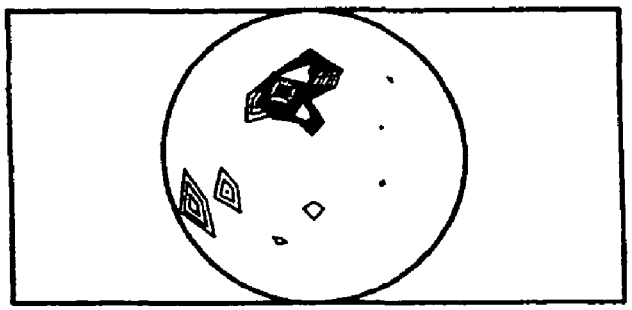
FIGS. 13(d), 13(e) and 13(f) represent results of initial estimation of current sources using initial resolution, where the radius is R=7.0, R=8.0 and R=9.0, respectively, that is, closer to the surface of the brain.
Figure 13E:
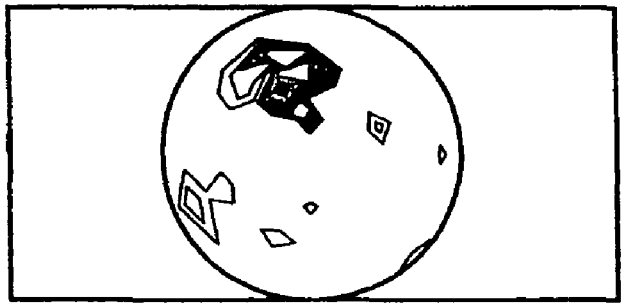
Figure 13F:
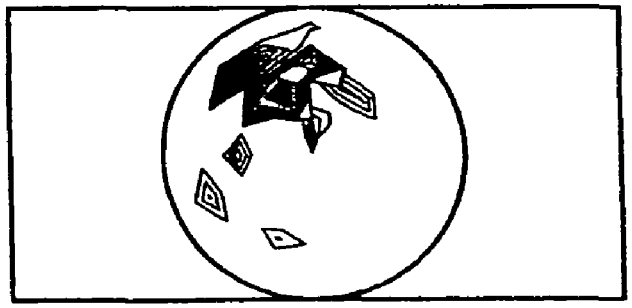

FIG. 13 represents results of initial estimation of current sources using initial resolution, where the radius is larger (that is, closer to the surface of the brain).

FIG. 13(d) shows the result where the radius is R=7.5, 13(e) shows the result where the radius is R=8.0 and 13(f) shows the result where the radius is R=9.0.

Figure 14:
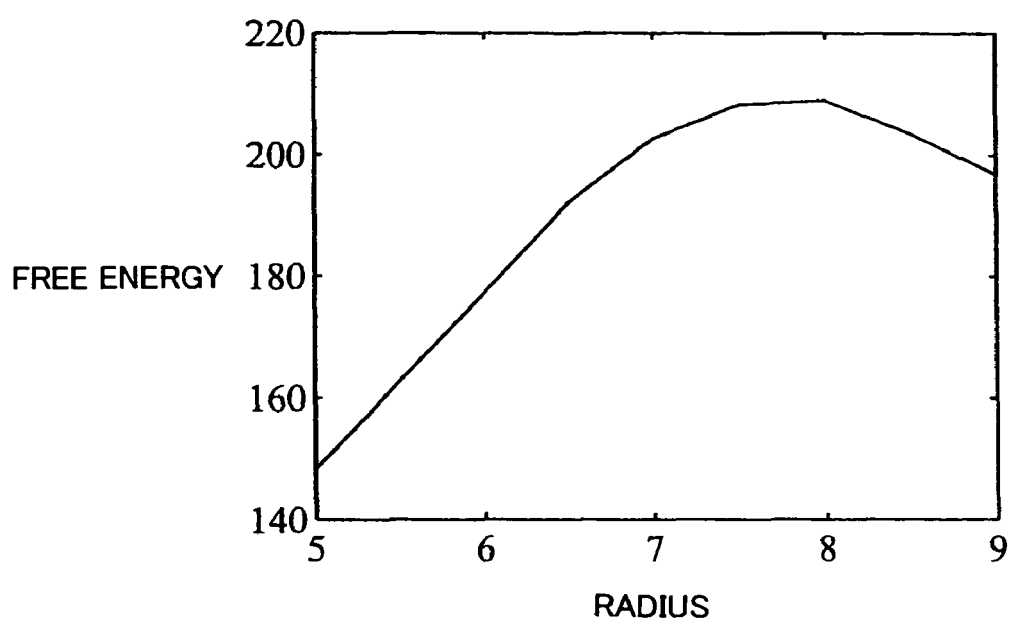
FIG. 14 represents magnitude of free energy on each virtual hemisphere, obtained when current distribution that attains highest free energy is calculated.

FIG. 14 represents magnitude of free energy on each virtual hemisphere, obtained when current distribution that attains maximum free energy is calculated for virtual hemispheres at various depths assumed in the brain.

Referring to FIG. 14, it can be understood that the maximum point of free energy exists between the radii of 7.0 and 8.0, when calculation is made assuming that the hemisphere as a whole is a virtual curved surface.

As can be seen from FIG. 13(d), one point of relative maximum exists in the current distribution on the virtual hemispherical surface having the radius of R=7.5.

As the current source is initially estimated using the initial resolution in this manner, on the virtual curved surface having the maximum free energy, a local surface that encompasses the relative maximum point of current distribution is calculated, and the process for identifying the current source is performed on the local surface.

FIGS. 15 and 16 represent processes for identifying the current source executed further on a local surface including a point of relative maximum, with the resolution of lattice points on the local surface and the resolution in the depth direction increased.

Figure 15A:
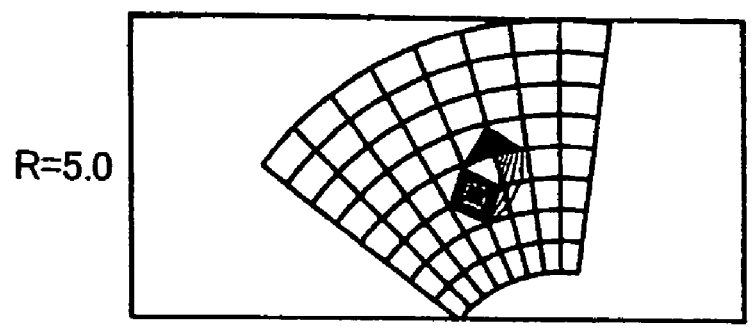
FIGS. 15(a), 15(b) and 15(c) represent processes for identifying the current source executed further on a local surface including a point of relative maximum, where the radius is R=5.0, R=6.0 and R=7.0, respectively.
Figure 15B:
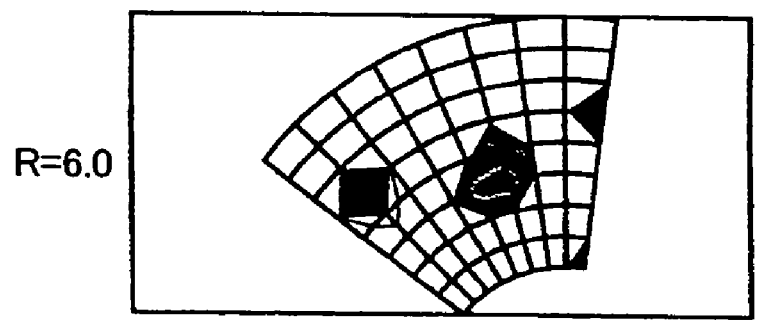
Figure 15C:
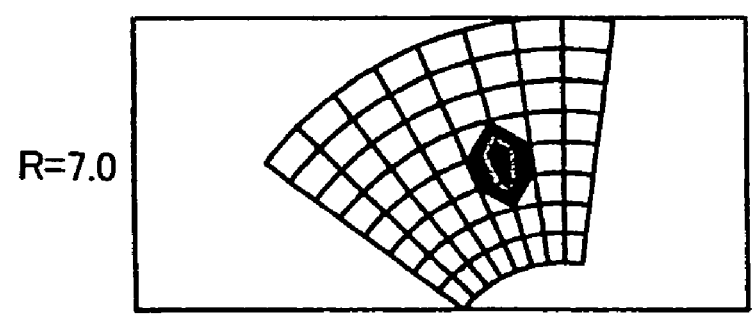
Figure 16D:
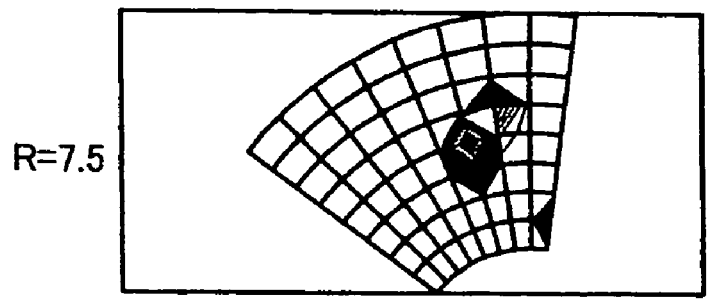
FIGS. 16(d), 16(e) and 16(f) represent processes for identifying the current source executed further on a local surface including a point of relative maximum, where the radius is R=7.5, R=8.0 and R=9.0, respectively.
Figure 16E:
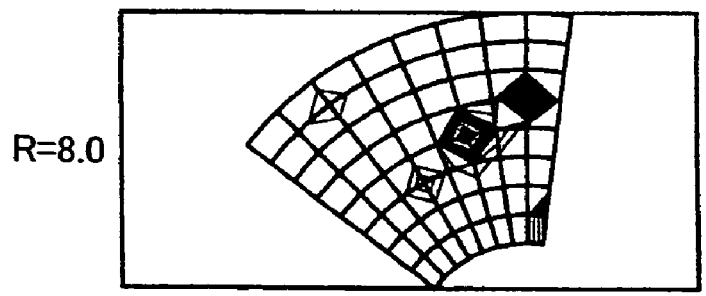
Figure 16F:
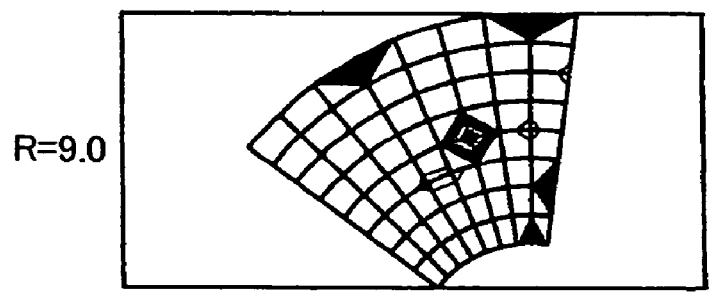

FIGS. 15(a), 15(b) and 15(c) represent current distribution on local surfaces where the radius is R=5.0, R=6.0 and R=7.0, respectively. Similarly, FIGS. 16(d), 16(e) and 16(f) represent current distribution on local surfaces where the radius is R=7.5, R=8.0 and R=9.0, respectively.

Figure 17:
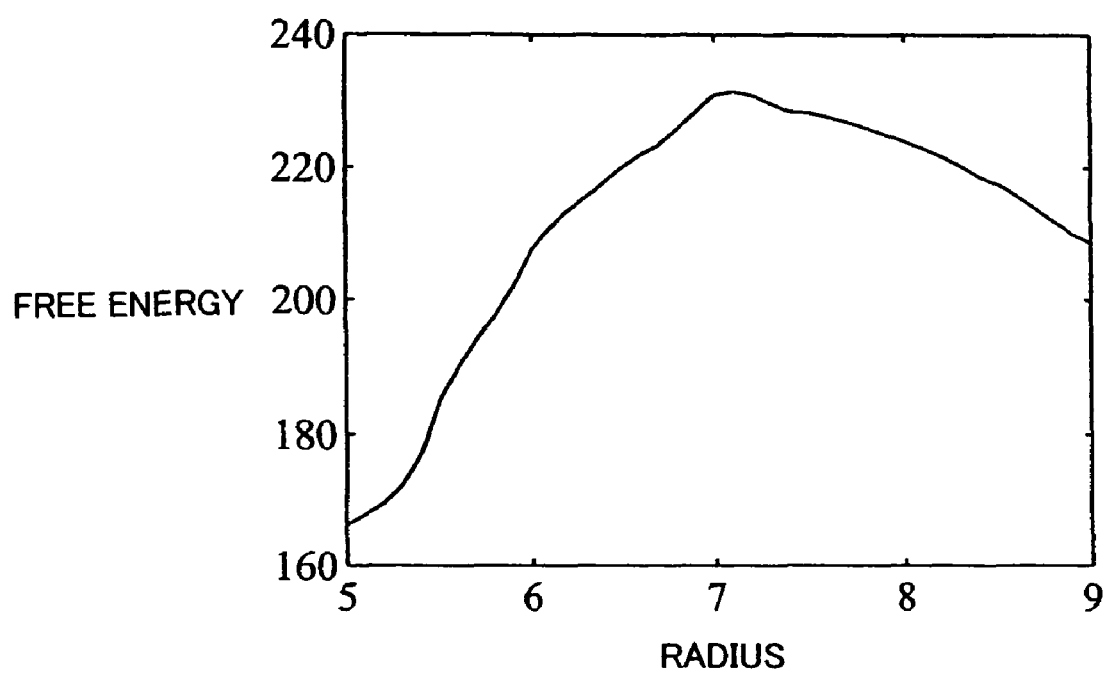
FIG. 17 represents the free energy calculated with the depth of local surface varied.

FIG. 17 represents the free energy calculated with the depth of local surface varied.

Referring to FIG. 17, the free energy as a result of calculation using the local surface has the relative maximum value near the radius of R=7, and from the result, it is possible to identify that one current source exists at the position of R=7.

The current distribution of the current source at this time is as shown in FIG. 15(c), and as already described, it can be understood that the current distribution also has the narrowest expansion.

Figure 18:
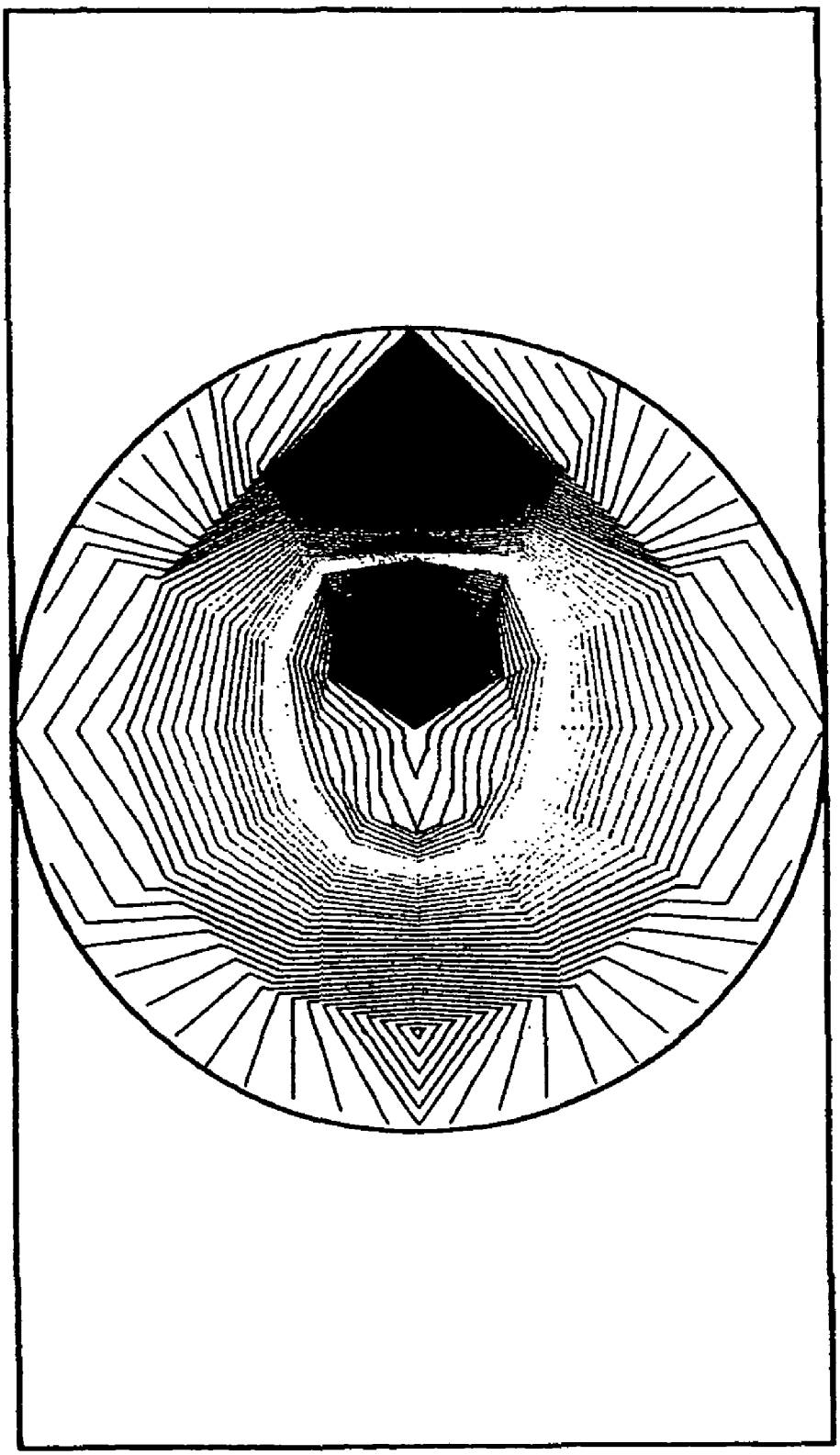
FIG. 18 is a top view of a magnetic field distribution observed on a surface of the human brain assumed as a hemisphere, when there are two current sources in the brain.

FIG. 18 is a top view of a magnetic field distribution observed on a surface of the brain assumed as a hemisphere, when there are two current sources in the brain.

In the example shown in FIG. 18, it is assumed that the current sources are positioned at the radii of R=6.0 and R=8.0.

FIGS. 19 and 20 represent results of initial estimation of current sources using initial resolution.

Specifically, FIGS. 19 and 20 illustrates the process (step S104) for performing initial estimation of current sources using the initial resolution shown in FIG. 4, when there are two current sources in the brain.

Figure 19A:
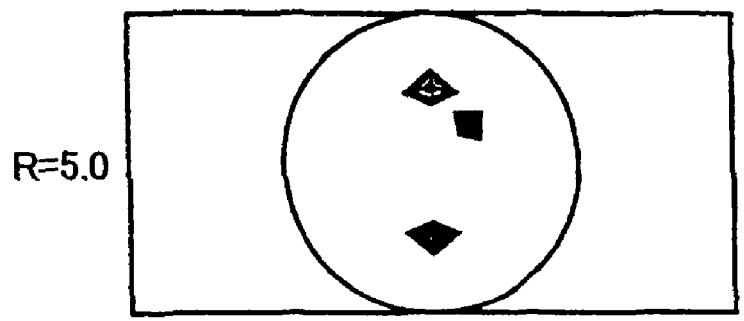
FIGS. 19(a), 19(b) and 19(c) represent results of initial estimation of current sources using initial resolution, where the radius is R=5.0, R=6.0 and R=7.0, respectively.
Figure 19B:
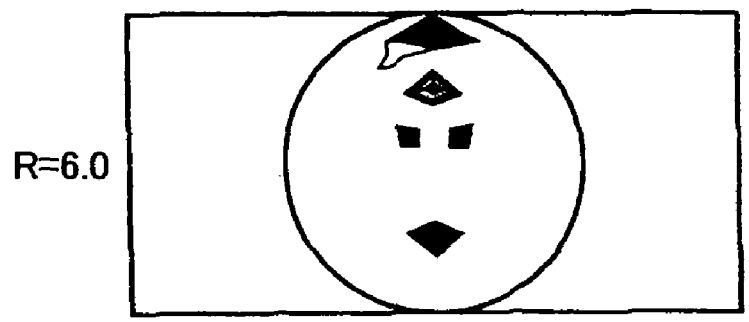
Figure 19C:
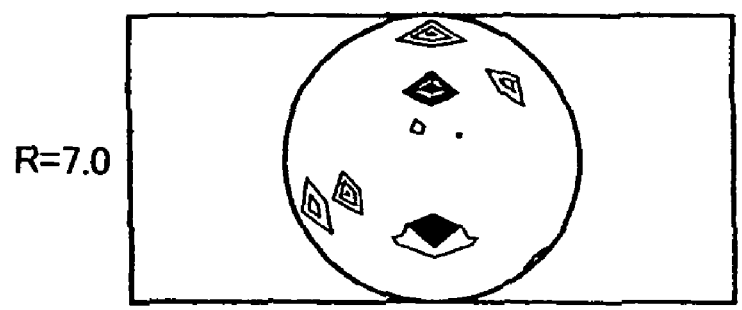

FIGS. 19(a), 19(b) and 19(c) represent current distribution on virtual hemispherical surfaces where the radius is R=5.0, R=6.0 and R=7.0, respectively.

Figure 20D:
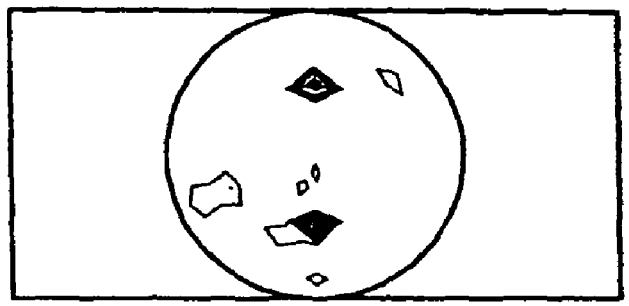
FIGS. 20(d), 20(e) and 20(f) represent results of initial estimation of current sources using initial resolution, where the radius is R=7.5, R=8.0 and R=9.0, respectively.
Figure 20E:
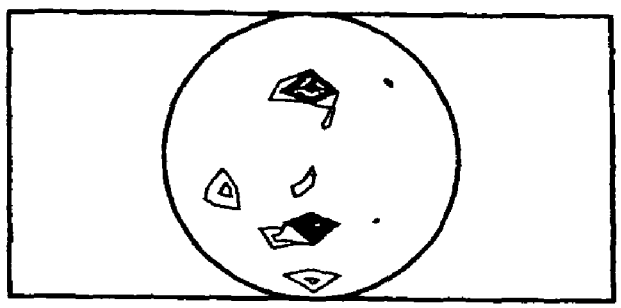
Figure 20F:
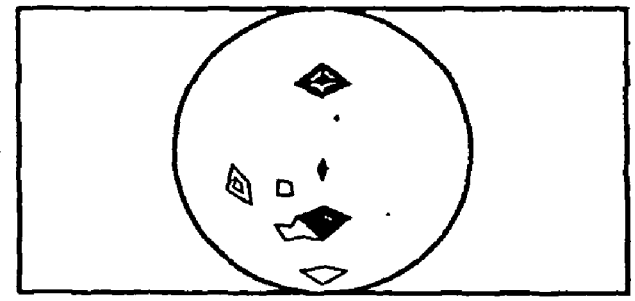

FIGS. 20(d), 20(e) and 20(f) represent current distribution on virtual hemispherical surfaces where the radius is R=7.5, R=8.0 and R=9.0, respectively.

Figure 21:
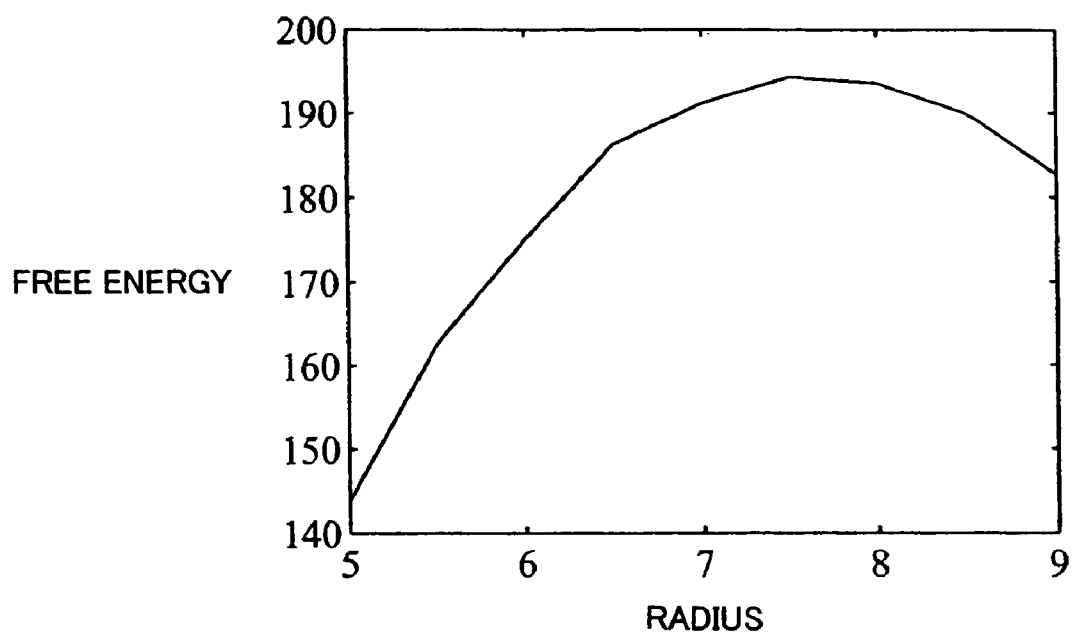
FIG. 21 represents radius dependency of free energy, when current distribution that attains highest free energy is calculated for each virtual hemispherical surface.

FIG. 21 represents radius dependency of free energy, when current distribution that attains maximum free energy is calculated for each virtual hemispherical surface of the whole hemispherical surfaces.

As shown in FIG. 21, when the free energy is calculated over the entire hemispherical surface, it is understood that the maximum value of free energy exists between the radii of R=7 and R=8, that is, near the radius of R=7.5.

As can be seen from FIG. 20(d), on the virtual hemispherical surface having the radius of R=7.5, there are two relative maximum points in the current distribution and two local surfaces are determined.

Next, the result of calculation corresponding to the process of step S1106 shown in FIG. 4 will be described.

FIGS. 22 and 23 illustrates the process for calculating the depth of a lth local surface $R_M(l)$ attaining maximum posterior probability, to identify a current source closest to the brain surface.

Therefore, FIGS. 22 and 23 represent current distribution when a local surface corresponding to one current source is moved while the other local surface is fixed on a surface that attains the maximum free energy calculated over the entire spherical surface.

Figure 22A:
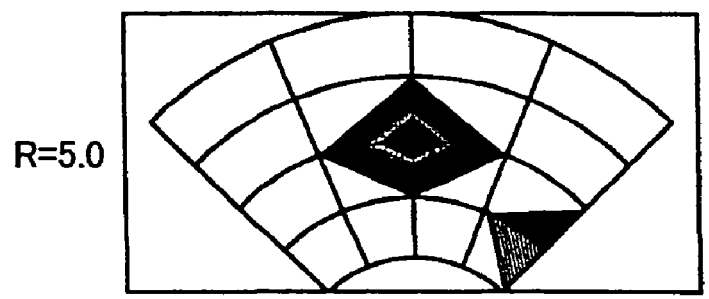
FIGS. 22(a), 22(b) and 22(c) represent current distribution on local surfaces where the radius is R=5.0, R=6.0 and R=7.0, respectively, illustrating the process for calculating the depth of a first local surface attaining maximum posterior probability, to identify a current source closest to the brain surface.
Figure 22B:
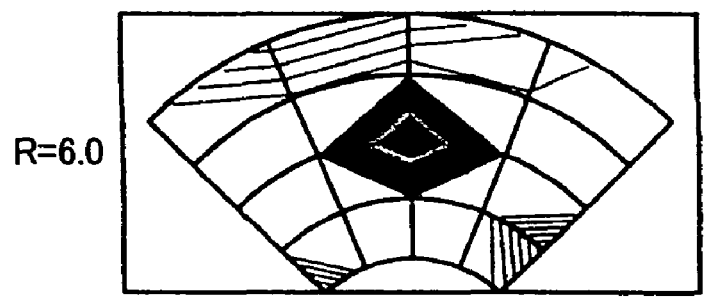
Figure 22C:
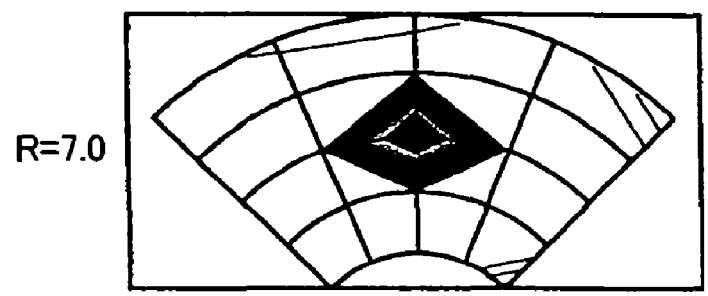

FIGS. 22(a), 22(b), 22(c) represent current distribution on local surfaces where the radius is R=5.0, R=6.0 and R=7.0, respectively.

Figure 23D:
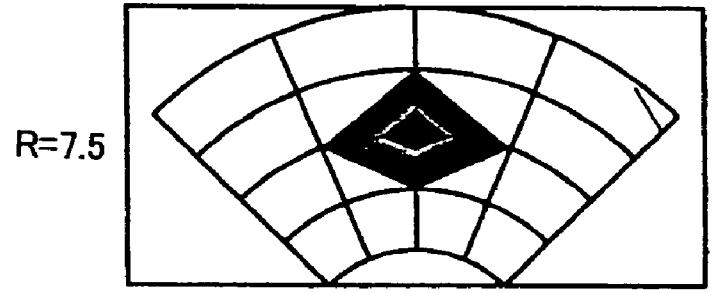
FIGS. 23(d), 23(e) and 23(f) represent current distribution on local surfaces where the radius is R=7.5, R=8.0 and R=9.0, respectively, illustrating the process for calculating the depth of a first local surface attaining maximum posterior probability, to identify a current source closest to the brain surface.
Figure 23E:
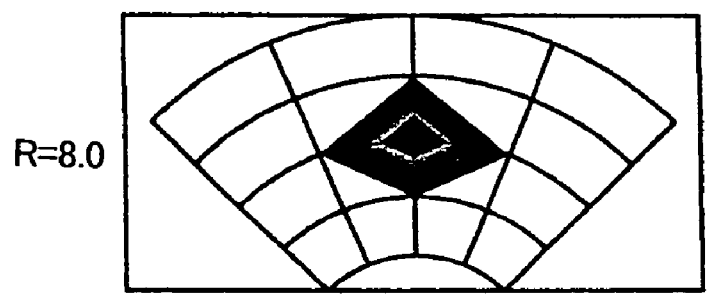
Figure 23F:
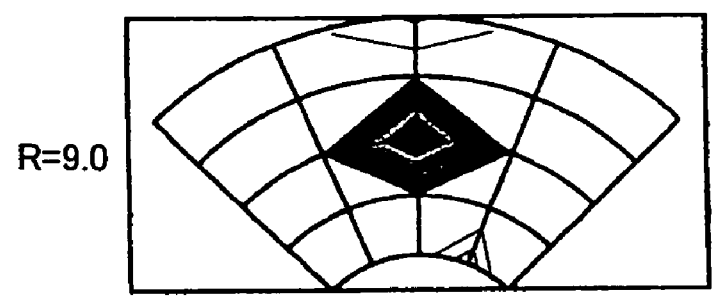

FIGS. 23(d), 23(e) and 23(f) represent current distribution on local surfaces where the radius is R=7.5, R=8.0 and R=9.0, respectively.

Figure 24:
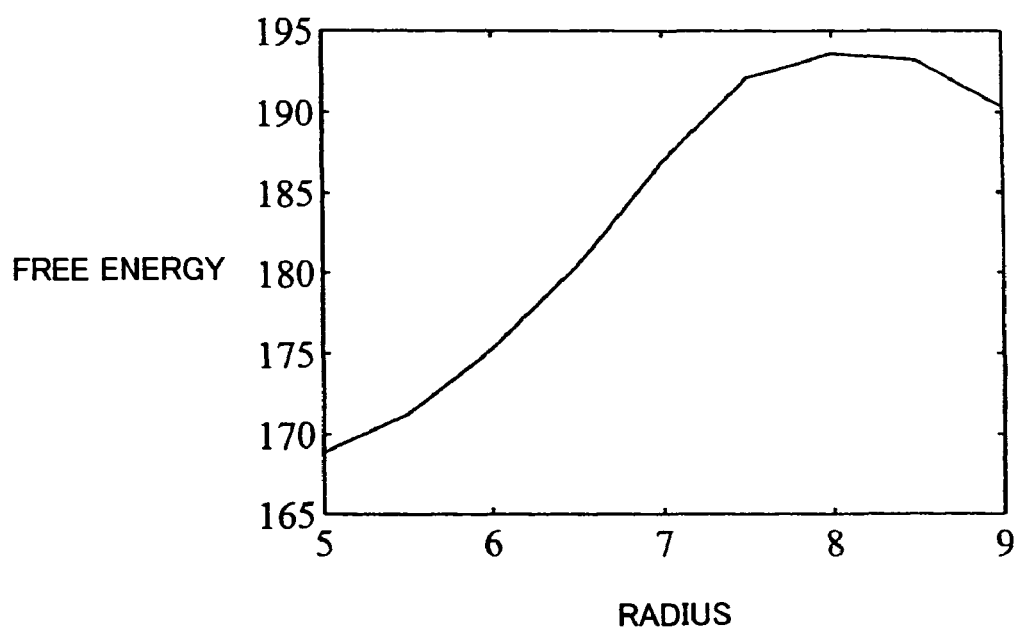
FIG. 24 represents local surface position (radius) dependency of free energy when a virtual local surface is moved.

FIG. 24 represents local surface position (radius) dependency of free energy when a virtual local surface is moved as shown in FIGS. 22 and 23.

As shown in FIG. 24, when a local surface corresponding to one current source is moved to the position of R=8 while the other local surface is fixed on a surface that attains the maximum free energy calculated over the entire spherical surface, the free energy is maximized.

Therefore, from the result shown in FIG. 24, it can be seen that the position of the current source closest to the brain surface is at the radius of R=8.0.

Thereafter, the depth of the other current source is identified.

Here, the depth of the local surface corresponding to one current source is fixed at the radius of R=8.0, and the depth of the local surface corresponding to the other current source is moved.

FIGS. 25 and 26 represent current distribution when one local surface is fixed on a specific surface and a local surface corresponding to the other current source is moved.

Figure 25A:
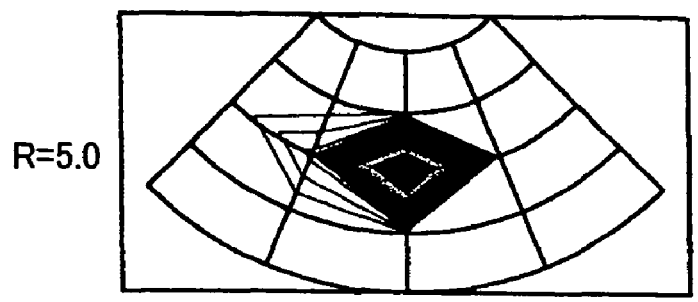
FIGS. 25(a), 25(b) and 25(c) represent current distribution on local surfaces where the radius is R=5.0, R=5.5 and R=6.0, when one local surface is fixed on a specific surface and a local surface corresponding to the other current source is moved.
Figure 25B:
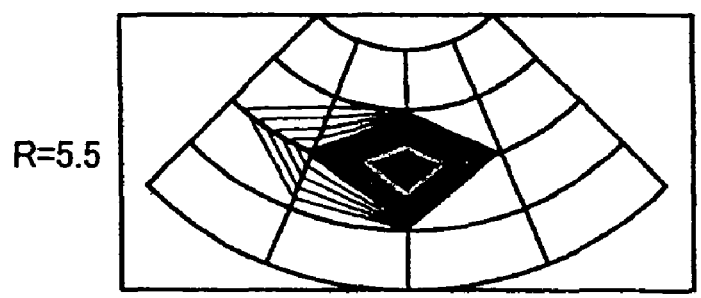
Figure 25C:
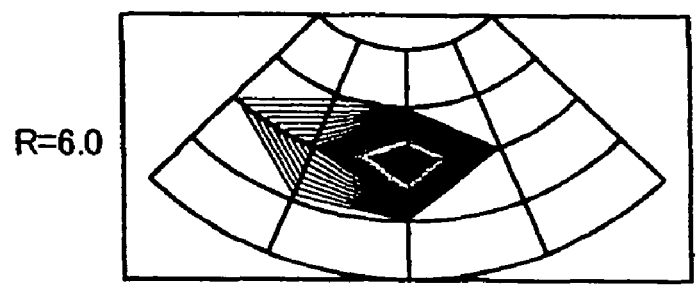

FIGS. 25(a), 25(b) and 25(c) represent current distribution on local surfaces where the radius is R=5.0, R=5.5 and R=6.0.

Figure 26D:
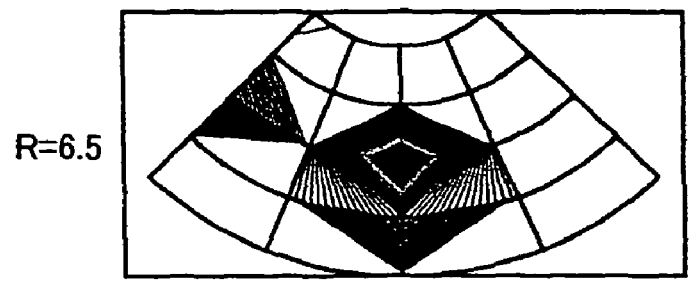
FIGS. 26(d), 26(e) and 26(f) represent current distribution on local surfaces where the radius is R=6.5, R=7.0 and R=7.5, when one local surface is fixed on a specific surface and a local surface corresponding to the other current source is moved.
Figure 26E:
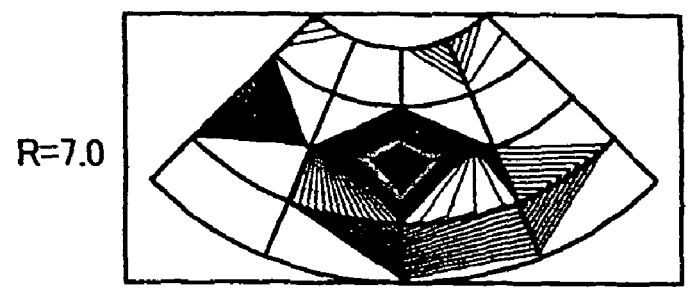
Figure 26F:
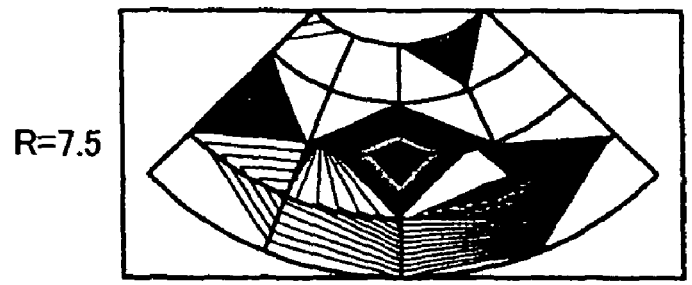

FIGS. 26(d), 26(e) and 26(f) represent current distribution on local surfaces where the radius is R=6.5, R=7.0 and R=7.5.

Figure 27:
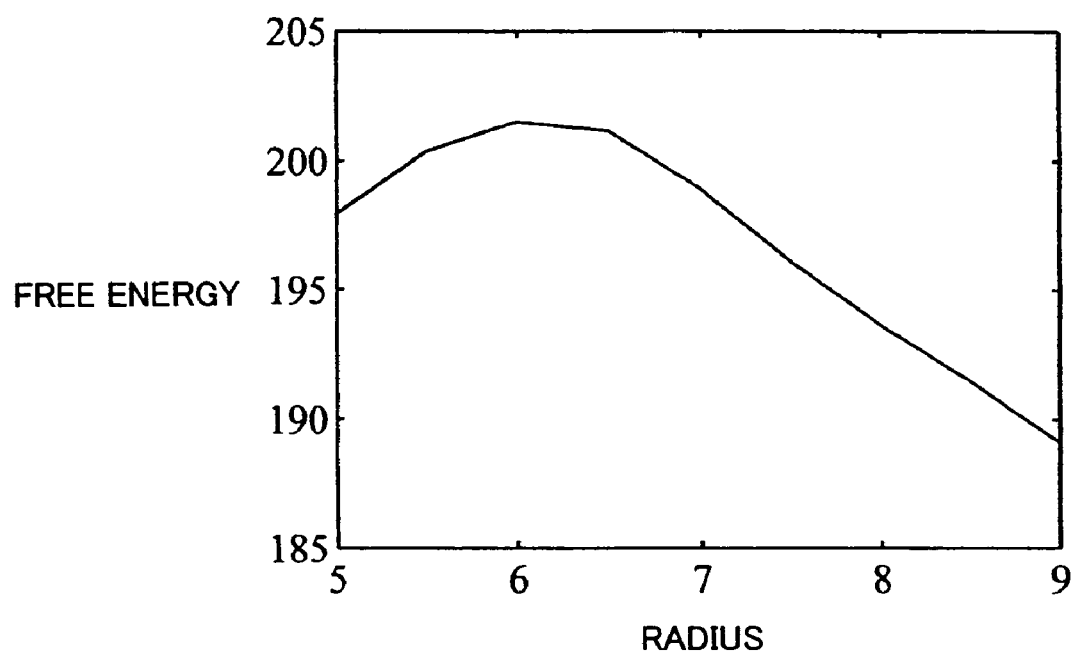
FIG. 27 represents local surface position (radius) dependency of free energy when a virtual local surface is moved.

FIG. 27 represents local surface position (radius) dependency of free energy when a virtual local surface is moved as shown in FIGS. 25 and 26.

As can be seen from FIG. 27, the free energy is maximized at the position of R=6.

It can be understood that by such a process, even when there are two current sources in the brain, it is possible to identify the depth of each of the current sources.

[Second Embodiment]

In the following, the second embodiment of the present invention will be described, in which, among the processes implemented by software (or partially by hardware) of the "brain current source estimating method," "brain current source estimating program," and "brain current source estimating apparatus" in accordance with the first embodiment of the present invention described above, the processes from "(I) Preparation for current source estimation" to "(3) Calculation of free energy" are modified.

As a background for describing the modifications in accordance with the second embodiment, the concept of the first embodiment will be summarized in the following, and of the basic concept, portions that are modified in the second embodiment will be described.

(Concept of Virtual Curved Surface Estimation in the First Embodiment)

In the first embodiment, as a current model on the virtual curved surface, current dipoles on lattice points are assumed, and a process of solving an inverse problem that the current distribution J is estimated from observed magnetic field B on the observation surface is performed. Here, such an inverse problem is a so called "ill-posed problem" and it is difficult to find an exact solution, as (the number of lattice points at which current dipoles exist) is generally larger than (the number of observation points).

In the first embodiment, in order to solve such a problem, the method of "Bayesian estimation" has been used.

Bayesian estimation utilizes the fact that posterior probability distribution when virtual surface M and observed magnetic field B are given can be represented by the following equation.

$$P(J|B, M) = \frac{P(B|J, M)P(J|M)}{P(B|M)}$$

Here, P(J|B,M) is the probability distribution on the virtual curved surface M under the condition that the magnetic field B has been observed, and it represents the "posterior probability distribution." P(B|J, M) is "data likelihood," P(J|M) is prior distribution and P(B|M) is marginal likelihood.

The marginal likelihood is given by

P(B|M)=∫dJP(B|J,M)P(J|M)

The posterior probability P(M|B) is given by $$P(M|B) = \frac{P(B|M)P(M)}{P(B)} \propto P(B|M)$$

Assuming that there is no prior information related to the depth, P(M)=constant, and therefore, the probability that the model M is the true model when the observation data B is given is in proportion to the model marginal likelihood P(M|B) under the assumption above, as already described with reference to the first embodiment.

Specifically, in the first embodiment, when the current model is selected, a model that attains the highest posterior probability, or the highest marginal likelihood, has been selected.

For such a process, the marginal log-likelihood log P(B|M) represented by the following equation is the object of calculation.

log P(B|M)=<log(P(B|J,M))>$_J$−KL(P(J|B,M)||P(J| M))=(expected log-likelihood)−(distance of prior/posterior distribution)~(recovery error)− (effective degree of freedom of parameters)

As represented by the equation above, that the marginal log-likelihood is maximized corresponds to a concept that the error and the effective degree of freedom of parameters are minimized, in other words, that the error and the expansion of current distribution are minimized.

In the first embodiment, the problem of maximizing the marginal log-likelihood described above has been solved by the so called "variational Bayes method" in which the trial posterior distribution Q is introduced as an approximation of the posterior distribution, and the posterior distribution is determined to maximize the free energy (O).

(Concept of Prior Distribution in the First Embodiment)

In the first embodiment, as a prior information of the brain current source, a localized condition that the current sources exist at a plurality of positions in the brain is used, which is represented in the form of hierarchical prior distribution. Specifically, hyper parameters $\alpha_n$(n=1, ..., N) are introduced and the form of the hierarchical prior distribution given by the following expressions are assumed.

$$P_0(J|\alpha, \beta) \propto \exp\left[-\frac{1}{2}\beta\sum_{n=1}^{N}\alpha_n|J_n|^2\right]$$

$$P_0(\alpha_n|\bar{\alpha}_0, \gamma_{\alpha 0}) \propto \exp[-\gamma_{\alpha 0}\alpha_n/\bar{\alpha}_0 + (\gamma_{\alpha 0} - 1)\log\alpha_n]$$

From the expressions above, it can be understood that the hyper parameter $\alpha n$ is in proportion to inverse variance (the reciprocal of variance) of current $J_n$. When the values of variance of current $J_n$ and inverse variance $\beta$ of noise are known in advance, a prior distribution may be used in which the value $\alpha_n$ is fixed to the value calculated from the values of variance of current and inverse variance of noise. The value of variance of the current, however, is generally unknown, and therefore, in the first embodiment, a hierarchical prior distribution $P_0(\alpha_n|\text{bar }\alpha_0 \gamma_{\alpha 0})$ for the hyper parameter $\alpha_n$ is assumed, and Bayesian estimation is performed on $\alpha_n$.

Here, bar $\alpha_n$ and $\gamma_{\alpha 0}$ are meta parameters for determining the shape of hierarchical prior distribution, and common values are assumed for every $\alpha_n$. When Bayesian estimation is performed using the localized condition hierarchical prior distribution, Bayesian estimation that recovers the observed data with smallest possible number of current dipoles is performed as described above.

Minimum norm estimation method, which is often used in current source estimation of MEG (Reference: M. S. Hämäläinen and R. J. Ilmoniem, Med. & Biol. Eng. & Comput., 32, 35-42, 1994) corresponds, from the view point of Bayesian estimation, to a process in which the value $\alpha_n$ as the prior distribution is made common to all the points, and the value is directly determined to be an appropriate value.

In the minimum norm estimation, total sum of current intensities at all the points is to be minimized, and hence points having small current intensities appear in large number in the estimated solution. Therefore, this method is disadvantageous in that it is difficult to determine whether such small current distributions represent the true current distribution or noise derived from estimation error.

The localized condition hierarchical prior distribution solves this problem of the minimum norm estimation method.

(Modifications in the Second Embodiment)

In the second embodiment, prior distribution considering not only the local condition but also continuous condition is assumed. When current source distribution is to be estimated with high precision with the spatial resolution in the order of millimeters, it is necessary to consider continuity of current distribution. Actually, neural cells in the cerebral cortex has a columnar structure having the radius of about 10 mm, and when a neural activity takes place, it is likely that neural cells in an area having the radius of about 20 mm fire simultaneously. Considering such points, in the second embodiment, a hierarchical prior distribution is assumed that combines the local condition and continuous condition, as will be described in the following.

In order to introduce the continuous condition, an internal variable Z is newly introduced, and the current J is represented as the internal variable Z smoothed through a smoothing filter W. Here, though not limiting, a Gauss filter may be used as such a smoothing filter W. Now, the prior distribution can be represented as $$P_0(J|Z, \alpha, \beta) \propto \exp\left[-\frac{1}{2}\beta\sum_{n=1}^{N}\alpha_n(J_n - W\cdot Z_n)^2\right]$$

$$P_0(Z|\lambda) \propto \exp\left[-\frac{1}{2}\beta\sum_{n=1}^{N}\lambda_n|Z_n|^2\right]$$

In the prior distribution above, integration of Z can be executed easily, as represented by $P_0(J|\alpha, \beta, \lambda) =$ $$\int dZ P_0(J|Z, \alpha, \beta)P_0(Z|\lambda) \propto \exp\left[-\frac{1}{2}\beta J'(A^{-1} + W\cdot\Lambda^{-1}\cdot W')^{-1}J\right]$$

where A and Λ represent diagonal matrixes having $\{\alpha_n | n = 1, \ldots, N\}$ and $\{\lambda_n | n=1, \ldots, N\}$ as diagonal components, respectively.

Specifically, assuming the prior distribution $P_0(J|Z, \alpha, \beta)P_0(Z|\lambda)$ by introducing the internal variable Z is the same as assuming the prior distribution that has a covariance matrix $\beta^{-1}(A^{-1} + W \cdot \Lambda^{-1} \cdot W')$ for the current J. It is easier, however, to apply variational Bayes method when the prior distribution is represented by using the internal variable Z. Therefore, the prior distribution will be represented by using the internal variable Z in the following. Further, the value of hyper parameter $\lambda_n$ is not known in advance as in the case of hyper parameter $\alpha_n$, Bayesian estimation is performed on $\alpha_n$ and $\lambda_n$, assuming the hierarchical prior distribution of the following form.

$$P_0(\alpha_n | \bar{\alpha}_{0n}, \gamma_{\alpha 0n}) \propto \exp[-\gamma_{\alpha 0n}\alpha_n/\bar{\alpha}_{0n} + (\gamma_{\alpha 0n}-1)\log \alpha_n]$$

$$P_0(\lambda_n | \bar{\lambda}_{0n}, \gamma_{\lambda 0n}) \propto \exp[-\gamma_{\lambda 0n}\lambda_n/\bar{\lambda}_{0n} + (\gamma_{\lambda 0n}-1)\log \lambda_n]$$

The hierarchical prior distribution extended in this manner encompasses the localized condition prior distribution of the first embodiment. Specifically, when the smoothing filter matrix W is identically 0, the hierarchical prior distribution combining the continuous condition and the localized condition coincides with the localized condition prior distribution of the first embodiment.

It is assumed that meta parameters bar $\alpha_{n0}$, $\gamma_{\alpha 0n}$, bar $\lambda_{0n}$ and $\gamma_{\lambda 0n}$ for determining the shape of hierarchical prior distribution may depend more generally on the positions of lattice points. When there is only the observation data of MEG (or EEG), there is no prior information related to these values. Therefore, as in the first embodiment, these parameters are substantially determined commonly without any dependence on the location of lattice points, as will be described in the following. When observation data obtained by other observation means is available, however, the values of meta parameters may be determined for each lattice point using such information, as will be described with reference to the third embodiment.

(Specific Calculation Procedure of the Second Embodiment)

The calculation procedure described in the following is in most part similar to that of the first embodiment. Therefore, in the following, description will be made mainly focusing on the modifications from the first embodiment.

First, as in the first embodiment, when a current distribution J on a virtual curved surface is given and the observed magnetic field is B, a model probability distribution $P(B|J, \beta)$ is given, using logarithmic representation, by the following equation.

$$\log P(B | J, \beta) = -\frac{1}{2}\beta |B - G \cdot J|^2 + \frac{1}{2}(I \cdot C)\log(\beta/2\pi)$$

observed magnetic field B: (I×C) dimensional vector
current distribution J: R dimensional vector, R=N×D, N: number of lattice points, D: number of components
lead field matrix: G(I×C)×R dimensional matrix

[Hierarchical Prior Distribution]

The hierarchical prior distribution in accordance with the second embodiment is represented by the following equations.

$$\log P_0(J | Z, \beta, \alpha) = -\frac{1}{2}\beta(J - WZ)'A(J - WZ) + \frac{D}{2}\sum_{n=1}^{N}\log(\beta\alpha_n/2\pi)$$

$$\log P(Z | \beta, \lambda) = -\frac{1}{2}\beta Z'\Lambda Z + \frac{D}{2}\sum_{n=1}^{N}\log(\beta\lambda_n/2\pi)$$

$$(A)(n, d; n', d') = \delta_{nn'}\delta_{dd'}\alpha_n$$

$$(\Lambda)(n, d; n', d') = \delta_{nn'}\delta_{dd'}\lambda_n$$

$$(n, n' : 1, \ldots, N; d, d' : 1, \ldots, D)$$

$$\log P_0(\alpha) = \sum_{n=1}^{N}[-\gamma_{\alpha 0n}\bar{\alpha}_{0n}^{-1}\alpha_n + (\gamma_{\alpha 0n} - 1)\log\alpha_n - \Phi_G(\gamma_{\alpha 0n}, \bar{\alpha}_{0n}^{-1})]$$

$$\log P_0(\lambda) = \sum_{n=1}^{N}[-\gamma_{\lambda 0n}\bar{\lambda}_{0n}^{-1}\lambda_n + (\gamma_{\lambda 0n} - 1)\log\lambda_n - \Phi_G(\gamma_{\lambda 0n}, \bar{\lambda}_{0n}^{-1})]$$

$$\log P_0(\beta | \tau) = -\gamma_{\beta 0}\tau\beta + (\gamma_{\beta 0} - 1)\log\beta - \Phi_G(\gamma_{\beta 0}, \tau)$$

$$\log P_0(\tau) = -\gamma_{\tau 0}\bar{\tau}_0^{-1}\tau + (\gamma_{\tau 0} - 1)\log\tau - \Phi_G(\gamma_{\tau 0}, \bar{\tau}_0^{-1})$$

$$\Phi_G(\gamma, \tau) = \log\Gamma(\gamma) - \gamma\log(\gamma\tau)$$

Here, as in the first embodiment, β represents inverse variance of noise.

[Calculation of Trial Posterior Distribution]

At this time, it is assumed that the trial posterior distribution is represented by the form of a product of $Q_J$, $Q_Z$ and $Q_\alpha$, such as $Q = Q_J(J, \beta)Q_Z(Z)Q_\alpha(\alpha, \lambda, \tau)$.

Then, the free energy F(Q) is maximized successively for each of $Q_J$, $Q_Z$ and $Q_\alpha$. First, in the first step, $Q_Z$ and $Q_\alpha$ are fixed, and F(Q) is maximized for $Q_J$, and the following equations result.

$$Q_J(J, \beta) = Q_J(J | \beta)Q_\beta(\beta)$$

$$\log Q_J(J | \beta) = -\frac{1}{2}\beta(J - \bar{J})'\Sigma(J - \bar{J}) + \frac{1}{2}\log|\Sigma| + \frac{1}{2}(I \cdot C)\log(\beta/2\pi)$$

$$\log Q_\beta(\beta) = -\gamma_\beta \bar{\beta}^{-1}\beta + (\gamma_\beta - 1)\log\beta - \Phi_G(\gamma_\beta, \bar{\beta}^{-1})$$

Next, in the second step, $Q_J$ and $Q_\alpha$ are fixed, and F(Q) is maximized for $Q_Z$, and the following equation results.

$$\log Q_Z(Z) = -\frac{1}{2}\bar{\beta}(Z - \bar{Z})'\sum_Z(Z - \bar{Z}) + \frac{1}{2}\log|\sum_Z| + \frac{1}{2}R\log(\bar{\beta}/2\pi)$$

Further, in the third step, $Q_J$ and $Q_Z$ are fixed, and F(Q) is maximized for $Q_\alpha$, and the following equations result.

$$Q_\alpha(\alpha, \lambda, \tau) = Q_\alpha(\alpha)Q_\lambda(\lambda)Q_\tau(\tau)$$

$$\log Q_\alpha(\alpha) = \sum_{n=1}^{N}[-\gamma_{\alpha n}\bar{\alpha}_n^{-1}\alpha_n + (\gamma_{\alpha n} - 1)\log\alpha_n - \Phi_G(\gamma_{\alpha n}, \bar{\alpha}_n^{-1})]$$

$$\log Q_\lambda(\lambda) = \sum_{n=1}^{N}[-\gamma_{\lambda n}\bar{\lambda}_n^{-1}\lambda_n + (\gamma_{\lambda n} - 1)\log\lambda_n - \Phi_G(\gamma_{\lambda n}, \bar{\lambda}_n^{-1})]$$

$$\log Q_\tau(\tau) = -\gamma_\tau \bar{\tau}^{-1}\tau + (\gamma_\tau - 1)\log\tau - \Phi_G(\gamma_\tau, \bar{\tau}^{-1})$$

The specific method of calculating unknown numbers in the equations above will be described later.

As in the first embodiment, a trial posterior distribution that attains the relative maximum of free energy F(Q) is found again through repetitive calculation in the second embodiment.

Specifically, by the procedure described below, the trial posterior distribution Q is calculated through the first to third steps, and this procedure is repeated until the value of free energy F(Q) converges. How to determine the constant term at this time will be described later.

(1) Procedure of the First Step (Referred to as J-Step)

Expected values of current J and inverse variance $\beta$, and variable $\gamma_\beta$ are calculated in accordance with the following equations.

$$\Sigma = G'G + \overline{A} = \sum_G + \overline{A}$$

$$\overline{J} = \sum^{-1}(G' \cdot B + \overline{A}W\overline{Z})$$

$$\gamma_\beta = (I \cdot C)/2 + R/2 + \gamma_{\beta 0}$$

$$\gamma_\beta \overline{\beta}^{-1} = \frac{1}{2}|B - G \cdot \overline{J}|^2 + \frac{1}{2}(\overline{J} - W\overline{Z})'\overline{A}(\overline{J} - W\overline{Z}) + \frac{1}{2}\overline{Z}'\Lambda\overline{Z} + \frac{R}{2}\overline{\beta}^{-1} + \gamma_{\beta 0}\overline{\tau}$$

(2) Procedure of the Second Step (Z-Step)

Thereafter, expected value of internal variable Z is calculated as follows.

$$\Sigma_Z = \overline{\Lambda} + W'\overline{A}W$$

$$\hat{\Sigma}_Z = I + (\overline{\Lambda}^{-1}W'\overline{A})W$$

$$\overline{Z} = \Sigma_Z^{-1}W'\overline{A}\overline{J}$$

(3) Procedure of the Third Step ($\alpha$-Step)

Thereafter, the following calculations are made for the hyper parameters $\alpha_n$, $\gamma_{\alpha n}$, $\lambda_n$, $\gamma_{\lambda n}$, $\gamma_\tau$.

$$\gamma_{\alpha n} = \frac{D}{2} + \gamma_{\alpha 0 n}$$

$$\gamma_{\alpha n}\overline{\alpha}_n^{-1} = \frac{1}{2}\overline{\beta}|\overline{J}_n - (W\overline{Z})_n|^2 +$$

$$\frac{1}{2}\sum_{d=1}^{D}\left[(\sum^{-1})(n.d; n.d) + \left(W\sum_Z^{-1}W'\right)(n, d; n, d)\right] + \gamma_{\alpha 0 n}\overline{\alpha}_{0n}^{-1}$$

$$\gamma_{\lambda n} = \frac{D}{2} + \gamma_{\lambda 0 n}$$

$$\gamma_{\lambda n}\overline{\lambda}_n^{-1} = \frac{1}{2}\overline{\beta}|\overline{Z}_n|^2 + \frac{1}{2}\sum_{d=1}^{D}(\sum_Z^{-1})(n.d; n.d) + \gamma_{\lambda 0 n}\overline{\lambda}_{0n}^{-1}$$

$$\gamma_\tau = \gamma_{\beta 0} + \gamma_{\tau 0}$$

$$\gamma_\tau\overline{\tau}^{-1} = \gamma_{\beta 0}\overline{\beta} + \gamma_{\tau 0}\overline{\tau}_0^{-1}$$

The trial posterior distribution Q can be calculated through the procedures (1) to (3) above.

[Calculation of Free Energy]

The free energy of the second embodiment is calculated in accordance with the following equation.

$$F = LP + H_J + H_Z + H_\alpha + H_\lambda + H_\beta + H_\tau$$

Expected log-likelihood LP and model complexity terms $H_J$, $H_Z$, $H_\alpha$, $H_\lambda$, $H_\beta$, $H_\tau$ are calculated as follows.

$$LP = -\frac{1}{2}\overline{\beta}|B - G \cdot \overline{J}|^2 - \frac{1}{2}Tr\left(\sum^{-1}G'G\right) + \frac{1}{2}(I \cdot C)(<\log\beta> - \log 2\pi)$$

$$<\log\beta> = \log\overline{\beta} + \psi(\gamma_\beta) - \log\gamma_\beta$$

$$H_J = \frac{1}{2}\left[\log\left|\overline{A}\sum^{-1}\right| - Tr\left(\overline{A}\sum^{-1}\right) + R\right] -$$

$$\frac{1}{2}\overline{\beta}(\overline{J} - W\overline{Z})'\overline{A}(\overline{J} - W\overline{Z}) - \frac{1}{2}Tr\sum_Z^{-1}W'\overline{A}W$$

$$H_\beta = \gamma_{\beta 0}[\log(\overline{\beta\tau}) - \overline{\beta\tau} + 1] + \Phi(\gamma_\beta, \gamma_{\beta 0})$$

$$H_Z = \frac{1}{2}\left[\log\left|\sum_Z^{-1}\right| - Tr(\sum_Z^{-1}) + R\right] - \frac{1}{2}\overline{\beta}\overline{Z}'\Lambda\overline{Z}$$

$$H_\alpha = \sum_{n=1}^{N}\gamma_{\alpha 0 n}[\log(\overline{\alpha}_n/\overline{\alpha}_{0n}) - (\overline{\alpha}_n/\overline{\alpha}_{0n}) + 1]$$

$$H_\lambda = \sum_{n=1}^{N}\gamma_{\lambda 0 n}[\log(\overline{\lambda}_n/\overline{\lambda}_{0n}) - (\overline{\lambda}_n/\overline{\lambda}_{0n}) + 1]$$

$$H_\tau = \gamma_{\tau 0}[\log(\overline{\tau}/\overline{\tau}_0) - (\overline{\tau}/\overline{\tau}_0) + 1]$$

In the second embodiment also, the posterior distribution P(J|B) corresponds to $Q_J$ that maximizes F(Q), and the marginal log-likelihood log(P(B)) corresponds to the maximized F(Q).

Through the above described procedure, it is possible to calculate the marginal log-likelihood log(P(B)) of a virtual curved surface of a certain depth. Other procedures are the same as those of the first embodiment, and therefore, description thereof will not be repeated.

[Meta Parameters of Hierarchical Prior Distribution]

Selection of meta parameters in the calculation of hierarchical prior distribution will be described.

When observation data obtained by other observation method is not available, the values of meta parameters are selected commonly, regardless of the lattice points, as in the first embodiment.

Specifically, bar $\tau_0$, $\Gamma_{\beta 0}$ and $\gamma_{\tau 0}$ can be selected in the same manner as in the first embodiment. Further, meta parameters bar $\alpha_{0n}$, $\gamma_{\alpha 0n}$, bar $\lambda_{0n}$ and $\gamma_{\lambda 0n}$ can be represented as $$\overline{\alpha}_{0n} = \overline{\lambda}_{0n} = \overline{\alpha}_0$$

$$\gamma_{\alpha 0n} = \gamma_{\lambda 0n} = \gamma_{\alpha 0}$$

Here, bar $\alpha_0$ and $\gamma_{\alpha 0}$ can be selected in the same manner as in the first embodiment.

(Third Embodiment)

In the first and second embodiments, the methods of estimating brain current sources have been described, assuming that observation data obtained by other observation method is not available.

Recently, however, various methods have been developed to observe neural activities in the brain, and it has been made possible to obtain observation data using a plurality of observing means under the same experimental conditions. Therefore, as the third embodiment, modifications from the first and second embodiments will be described, where observation data obtained by other observation methods such as MI, fMRI or PET are available.

First, when MRI observation data for the same person is available, it is possible to obtain information related to the position of cerebral cortex or positions of other portions of the brain from MRI images. In such a case, it is possible to have the shape of virtual curved surface assumed in the first and second embodiments conforming to the shape of the cerebral cortex or the shape of other portions of the brain.

Further, when it is confirmed that a neural activity under certain experimental conditions takes place in the cerebral vertex, it is possible to omit searching in the depth direction and to estimate current distribution by placing lattice points only on the cerebral cortex.

By fMRI or PET, it is possible to obtain information related to the location of neural activities. One must be careful, however, in handling such information, because what is measured by fMRI is the amount of blood flow and what is measured by PET is the amount of radio isotope. Though these are considered to increase at portions having higher neural activities, what is measured is not the current intensity derived from the neural activities.

It is considered that the degree of activities measured by f and PET are co-related to some extent to the current intensity derived from neural activities. It is not clear, however, whether the correlation is linear or non-linear. Further, MEG and EEG have temporal resolution in the order of milliseconds, while fMRI has temporal resolution in the order of seconds, and PET in the order of several tens of seconds. Specifically, what is obtained by fMRI or PET is an average over a long period of time of the measured results of MEG or EEG.

Dale et al. proposes a method of utilizing the result of observation of MRI, fMRI or PET for the current source estimation by MEG or EEG in Reference: A. M. Dale et al., Neuron. 26, pp.55-67 (2000). In this method, however, the activity information of fMRI or the like is directly applied as variance information of current.

From the view point of Bayesian estimation in accordance with the present invention, this corresponds to direct designation of the value of inverse variance hyper parameter $\alpha_n$. As described above, however, the information obtained by fMRI or the like is not related directly to the current, and from the temporal view point, it is an average over a long period of time of the activities measured by MEG or EEG.

In contrast, in accordance with the present invention, the information obtained by fMRI or the like is not directly designated as the variance information of current but designated at the level of meta parameters of hierarchical prior distribution. Meta parameters $\gamma_{\alpha 0n}$ and $\gamma_{\lambda 0n}$ are meta parameters that control reliability of information given by the hierarchical prior distribution. Specifically, the smaller the values $\gamma_{\alpha 0n}$ and $\gamma_{\lambda 0n}$, the lower the reliability, and the higher the values $\gamma_{\alpha 0n}$ and $\gamma_{\lambda 0n}$, the higher the reliability.

As described with reference to the second embodiment, the hierarchical prior distribution in which localized condition and continuous condition are combined is the same as assuming $\beta^{-1}(A^{-1}+W \cdot \Lambda^{-1} \cdot W')$ as the covariance matrix of current of the prior distribution, where A and $\Lambda$ are diagonal matrixes having $\{\alpha_n | n=1, \ldots, N\}$ and $\{\lambda_n | n=1, \ldots, N\}$ as diagonal components, respectively.

Specifically, when the value $\alpha_n$ is smaller, the current comes to have larger variance, and when the value $\lambda_n$ becomes smaller, the covariance component derived from the continuous condition of current becomes larger. Meta parameters bar $\alpha_{0n}$ and bar $\lambda_{0n}$ represent expected values of $\alpha_n$ and $\lambda_n$ when there is no observation data obtained from MEG (or EEG).

When it is expected that neural activity is vigorous at a current lattice point n from fMRI or other observation method, the values of meta parameters bar $\alpha_{0n}$ and bar $\lambda_{0n}$ are made smaller, and bias information may be entered to facilitate the current at this current lattice point to assume a larger value.

In this manner, by introducing measured amount or information obtained by other observation method having different temporal scale at the level of meta parameters of hierarchical prior distribution, it becomes possible to enter information of other observation means as ambiguous information.

(Simulation Results)

Simulation results in accordance with the second and third embodiments will be described.

In the following, an area including a certain visual cortex at a back portion of cerebral cortex obtained by MRI image of a person is used as a virtual curved surface, and the search in the depth direction is omitted.

As for the simulation data, currents having the current intensity of (1.0, 1.0, 0.5) (arbitrary unit) and currents having the current intensity of (1.0, 0.0, 0.5) are caused to flow to areas V1, V2 and V5 in the visual cortex, magnetic fields formed by these currents on the MEG sensor are calculated, and Gaussian noise having the S/N ratio of 0.1 is added thereto, to provide the observation data.

Figure 28:
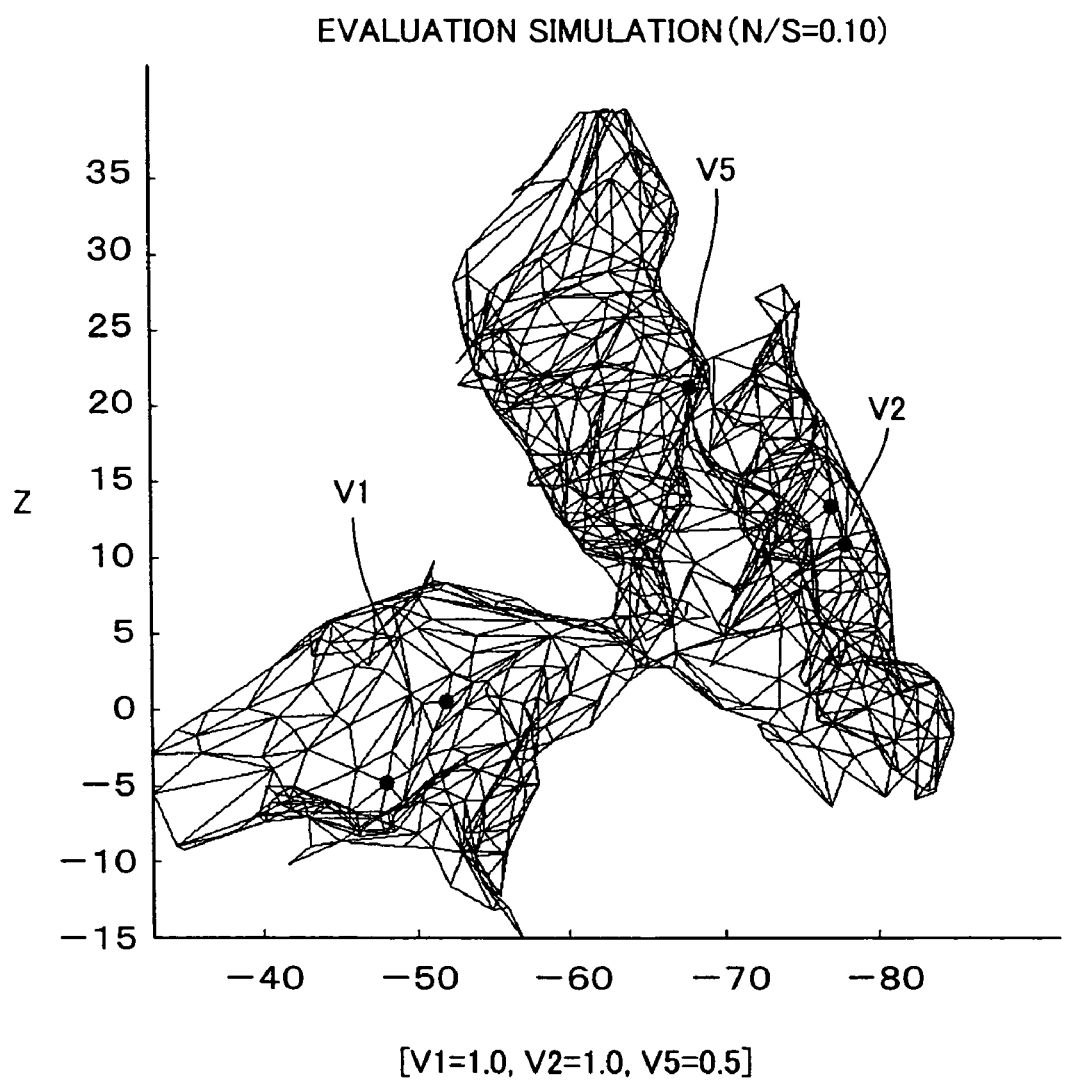
FIG. 28 is a first graph representing a result of simulation considering localized condition only.
Figure 29:
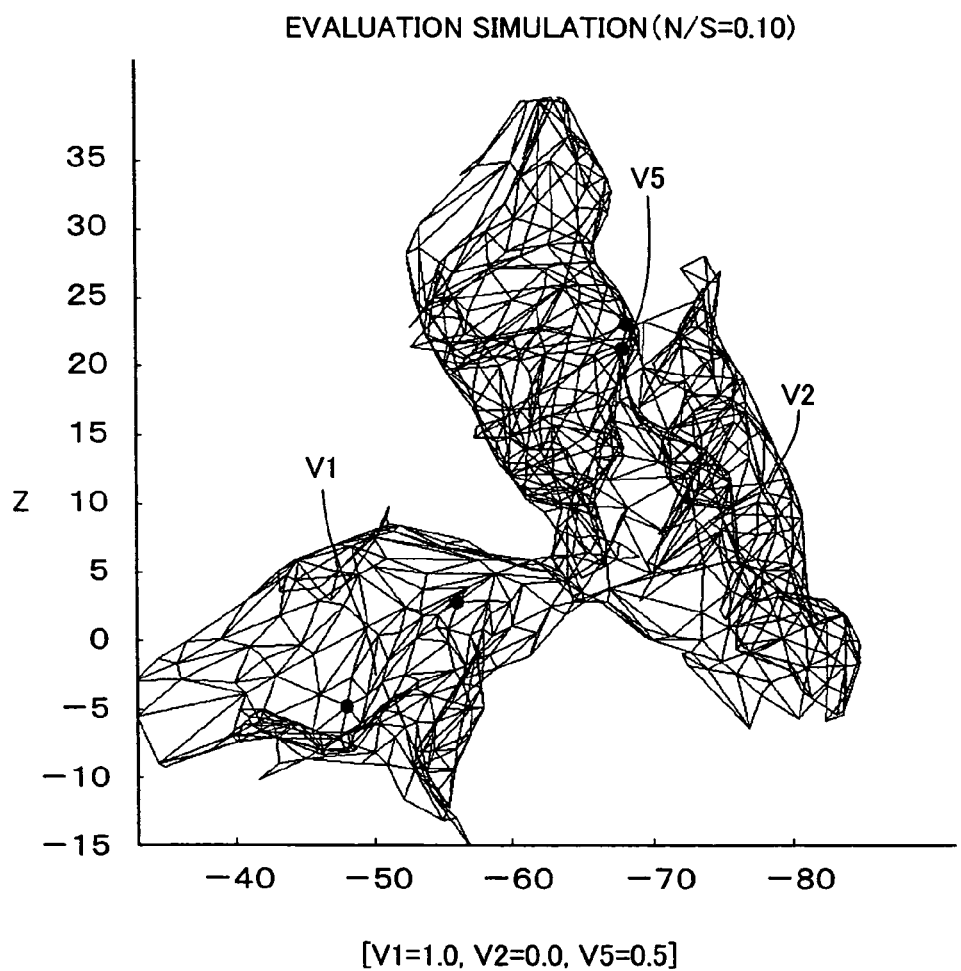
FIG. 29 is a second graph representing a result of simulation considering localized condition only.

FIGS. 28 and 29 represent results of Bayesian estimation considering localized condition only. In the figures, a vertex of each triangle represents a lattice point prepared on the virtual curved surface, and a current dipole is allocated to each lattice point. The interval between each of the lattice points is about 3 mm in average, and spatial resolution is high. Further, the virtual curved surface has a complicated three dimensional shape as it is a separated part of cerebral cortex. The figures are two-dimensional projection of the three dimensional shape. In the figures, reference characters V1, V2 and V5 denote the areas V1, V2 and V5 of the visual cortex. In the figures, black circles represent points having high estimated current intensity.

Figure 30:
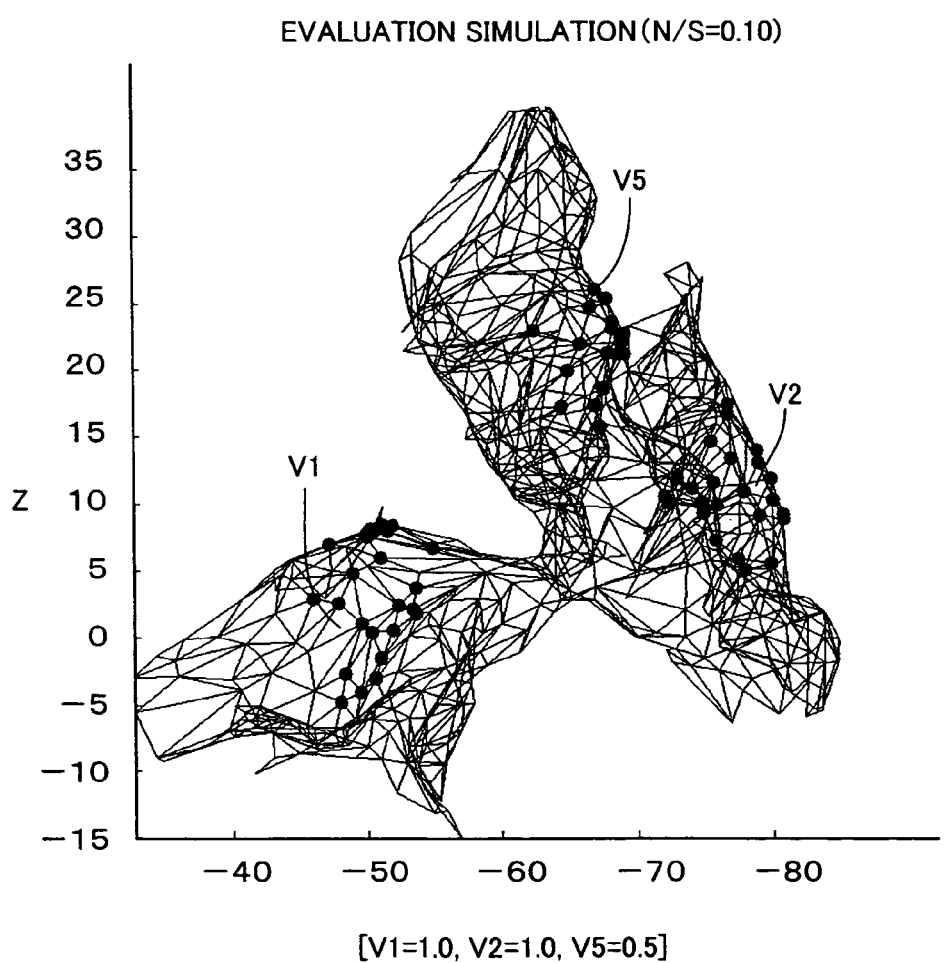
FIG. 30 is a first graph representing a result of simulation considering both continuous condition and localized condition.
Figure 31:
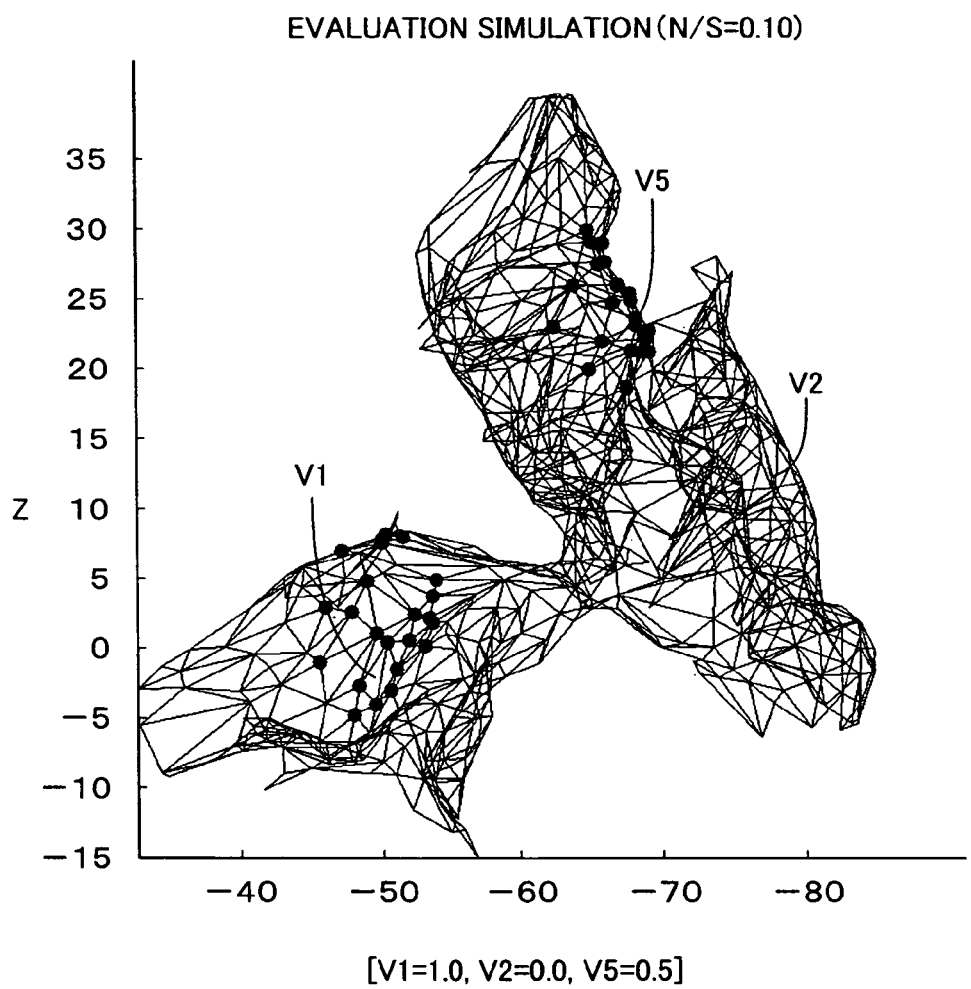
FIG. 31 is a second graph representing a result of simulation considering both continuous condition and localized condition.

FIGS. 30 and 31 represent result of Bayesian estimation considering both continuous condition and localized condition. The results of estimation recover the position and expansion of current distribution of almost true values. As can be seen from FIGS. 28 and 29, when Bayesian estimation is made using localized condition, the position of the current is correctly estimated, whereas the expansion of the current is estimated to be too small. From this simulation, it is appreciated that introduction of continuous condition is effective when spatial resolution is high.

Next, a simulation was made with the S/N ratio of noise increased to 0.2 and the current distribution unchanged. In that case, even when hierarchical prior distribution combining the localized condition and continuous condition was used, the expansion of current distribution could not be recovered, because of the influence of severe noise.

Thereafter, a simulation was made assuming that information of observation data obtained by other observation means is available under the bad condition as above. In the simulation, it was assumed that information indicating that activities in areas V1, V2 and V5 are vigorous is obtained from the observation data of fMRI. Considering the fact that the active areas of fMRI do not always correspond to current activities and that fMRI corresponds to an average over a long period of time of MEG observed data, it was assumed that the areas indicating high activities in fMRI were areas V1, V2 and V5 expanded by about 20 mm in radius. The same fMRI information was used when the current intensities at V1, V2 and V5 were (1.0, 1.0, 0.5) and (1.0, 0.0, 0.5), respectively.

By the setting above, a situation is simulated in which the active area of fMRI does not always correspond to the current intensity, though it is correlated to some extent. Under such setting, meta parameter of lattice points corresponding to the active area of fMRI was set to bar $\alpha_{0n}$=bar $\lambda_{0n}$=2×Tr(G'·G)/ tilde N, and meta parameter of other lattice points was set to bar $\alpha_{0n}$=bar $\lambda_{0n}$=50000×Tr(G$^t$·G)/tilde N. Here, the term "tilde" preceding a variable means that the variable has the sign "~" thereabove.

The values of $\gamma_{\alpha 0n}$ and $\gamma_{\lambda 0n}$ were commonly set to $\gamma_{\alpha 0n}$=$\gamma_{\lambda 0n}$=0.1 for all points.

Figure 32:
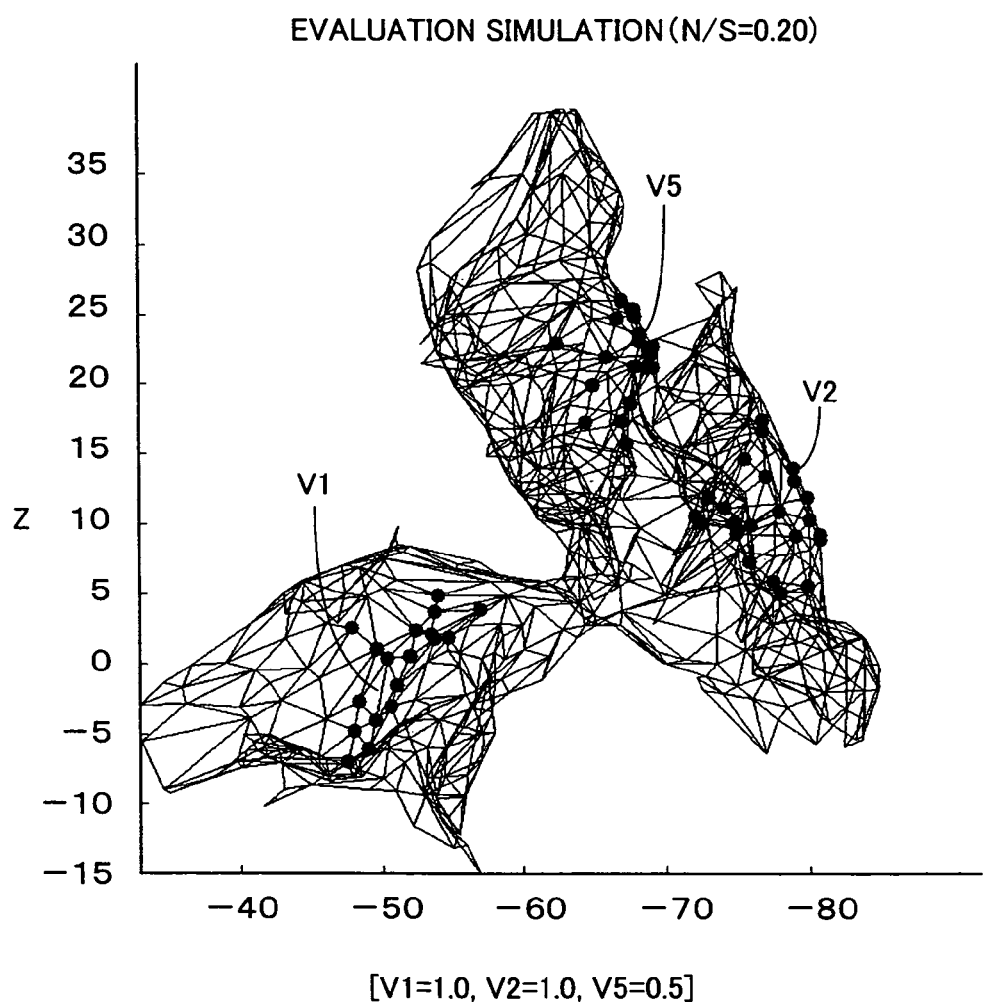
FIG. 32 is a first graph representing a result of simulation considering both continuous condition and localized condition, and using-hierarchical prior distribution that facilitates estimation of a current in a region where presence of a current source is highly likely.
Figure 33:
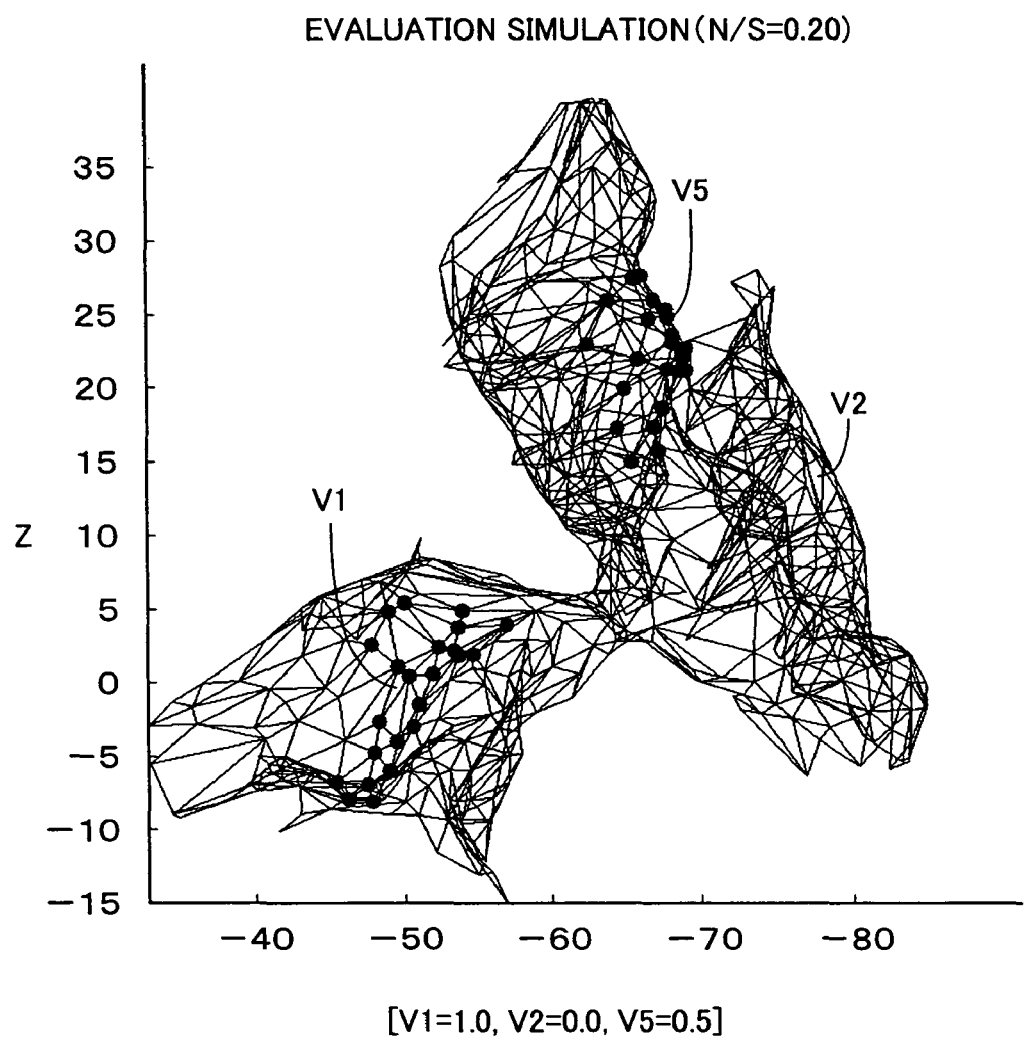
FIG. 33 is a second graph representing a result of simulation considering both continuous condition and localized condition, and using hierarchical prior distribution that facilitates estimation of a current in a region where presence of a current source is highly likely.

FIGS. 32 and 33 represent the results of estimation at this time. From these figures, it can be understood that even when there is considerable noise, correct estimation is possible by adding information obtained by other observation means.

Although the present invention has been described in detail, it is clearly understood that the same is by way of illustration only and is not to be taken by way of limitation, the spirit and scope of the present invention being limited only by the terms of the appended claims.

The invention claimed is:

1. A computer-implemented brain current source estimating method for estimating, based on an electromagnetic field observed outside a scalp, a position of a current source as a source of said electromagnetic field existing in a brain, comprising the steps of
receiving measurements of an observed electromagnetic field observed outside a scalp;
setting, in a computer simulation of the brain, a plurality of computer simulated curved surfaces having depths from brain surface different from each other and shapes not intersecting with each other, and setting lattice points on each of said computer simulated curved surfaces;
automatically estimating, on each of said computer simulated curved surfaces, a current distribution for recovering said observed electromagnetic field, wherein said step of automatically estimating a current distribution includes a step of setting, when said current distribution is estimated in accordance with variational Bayesian estimation, a hierarchical prior distribution representing a localized condition of said current source in said variational Bayesian estimation;
based on an expansion of the current distribution estimated on each one of said computer simulated curved surfaces and a difference between an electromagnetic field recovered based on said current distribution and said observed electromagnetic field, identifying one computer simulated curved surface among said plurality of computer simulated curved surfaces as a true curved surface on which said current source exists, so that said expansion and said difference attain relative minimums at said identified computer simulated curved surface; and
outputting a position corresponding to said identified computer simulated curved surface as the position of said current source, wherein
the above steps are performed by one or more computers programmed to perform the above steps.

2. The brain current source estimating method according to claim 1, wherein
said step of automatically estimating said current distribution includes the step of
determining posterior probability by Bayesian estimation method from prior distribution and observation data of said electromagnetic field; and
said step of identifying as a true curved surface on which said current source exists includes the step of
identifying a computer simulated curved surface of which corresponding said posterior probability attains the maximum, among said computer simulated curved surfaces.

3. The brain current source estimating method according to claim 2, wherein
said step of automatically estimating a current distribution includes the step of
identifying a first computer simulated curved surface closest to said brain surface and having posterior probability attaining a relative maximum, among said plurality of computer simulated surfaces, while successively moving from a computer simulated curved surface on the side of the brain surface to a deeper side; and
said step of identifying a curved surface as a true curved surface on which said current source exists includes the steps of
identifying a localized current distribution corresponding to a point of relative maximum of said current distribution, on said first computer simulated curved surface,
separating a plurality of local surfaces each including said localized current distribution, and
fixing, among said plurality of local surfaces, local surfaces other than a local surface as an object of identification, moving said local surface as an object of identification in the depth direction, and identifying positions where said posterior probability attains the relative maximum, successively from the side closer to said brain surface.

4. The brain current source estimating method according to claim 3, wherein
in said step of automatically estimating a current distribution, said current distribution is estimated with a first spatial resolution;
said method further comprising the step of
re-estimating said current distribution with a second spatial resolution higher than said first resolution and resolution of said plurality of computer simulated curved surfaces in the depth direction being improved.

5. The brain current source estimating method according to claim 1, wherein
said step of setting a hierarchical prior distribution includes the step of
setting the hierarchical prior distribution using observation data obtained by other observation method independent of said observation of electromagnetic field for said estimation of the current source.

6. A brain current source estimating apparatus for estimating, based on an electromagnetic field observed outside a scalp, a position of a current source as a source of said electromagnetic field existing in a brain, comprising:
measurement receiving means for receiving measurements of an observed electromagnetic field observed outside a scalp;
computer simulated curved surface setting means for setting, in a computer simulation of the brain, a plurality of computer simulated curved surfaces having depths from brain surface different from each other and shapes not intersecting with each other, and setting lattice points on each of said computer simulated curved surfaces;
current distribution estimating means for automatically estimating, on each of said computer simulated curved surfaces, a current distribution for recovering said observed electromagnetic field, wherein
said current distribution estimating means includes condition setting means for setting, when said current distribution is estimated in accordance with variational Bayesian estimation, a hierarchical prior distribution representing a localized condition of said current source in said variational Bayesian estimation; and
current source identifying means for selectively identifying, based on an expansion of the current distribution estimated on each one of said computer simulated curved surfaces and a difference between an electromagnetic field recovered based on said current distribution and said observed electromagnetic field, one computer simulated curved surface among said plurality of computer simulated curved surfaces as a true curved surface on which said current source exists, so that said expansion and said difference attain relative minimums at said identified computer simulated curved surface.

7. The brain current source estimating apparatus according to claim 6, wherein
said automatic current distribution estimating means includes
posterior probability determining means for determining posterior probability by Bayesian estimation method from prior distribution and observation data of said electromagnetic field; and
said current source identifying means includes
computer simulated curved surface identifying means for identifying a computer simulated curved surface of which corresponding said posterior probability attains the maximum, among said computer simulated curved surfaces.

8. The brain current source estimating apparatus according to claim 7, wherein
said automatic current distribution estimating means includes
shallowest computer simulated curved surface identifying means for identifying a first computer simulated curved surface closest to said brain surface and having posterior probability attaining a relative maximum, among said plurality of computer simulated surfaces, while successively moving from a computer simulated curved surface on the side of the brain surface to a deeper side; and
said current source identifying means includes
localized current distribution identifying means for identifying a localized current distribution corresponding to a point of relative maximum of said current distribution, on said first computer simulated curved surface,
local surface extracting means for separating a plurality of local surfaces each including said localized current distribution, and
local surface position identifying means for fixing, among said plurality of local surfaces, local surfaces other than a local surface serving as an object of identification, moving said local surface as an object of identification in the depth direction, and identifying positions where said posterior probability attains the relative maximum, successively from the side closer to said brain surface.

9. The brain current source estimating apparatus according to claim 8, wherein
said automatic current distribution estimating means estimates said current distribution with a first spatial resolution and thereafter re-estimates said current distribution with a second spatial resolution higher than said first resolution and resolution of said plurality of computer simulated curved surfaces in the depth direction being improved.

10. The brain current source estimating apparatus according to claim 6, wherein
said condition setting means sets the hierarchical prior distribution using observation data obtained by other observation method independent of said observation of electromagnetic field for said estimation of the current source.

11. A computer readable storage medium storing program code for causing a computer to estimate, based on an electromagnetic field observed outside a scalp, a position of a current source as a source of said electromagnetic field existing in a brain, the program code causing the computer to perform a method comprising the steps of:
receiving measurements of an observed electromagnetic field observed outside a scalp;
setting, in a computer simulation of the brain, a plurality of computer simulated curved surfaces having depths from brain surface different from each other and shapes not intersecting with each other, and setting lattice points on each of said computer simulated curved surfaces;
automatically estimating, on each of said computer simulated curved surfaces, a current distribution for recovering said observed electromagnetic field, wherein
said step of automatically estimating a current distribution includes a step of setting, when said current distribution is estimated in accordance with variational Bayesian estimation, a hierarchical prior distribution representing a localized condition of said current source in said variational Bayesian estimation;
based on an expansion of the current distribution estimated on each one of said computer simulated curved surfaces and a difference between an electromagnetic field recovered based on said current distribution and said observed electromagnetic field, selectively identifying one computer simulated curved surface among said plurality of computer simulated curved surfaces as a true curved surface on which said current source exists, so that said expansion and said difference attain relative minimums at said identified computer simulated curved surface; and
outputting a position corresponding to said identified computer simulated curved surface as the position of said current source.

12. The computer readable storage medium according to claim 11, wherein
said step of automatically estimating said current distribution includes the step of
determining posterior probability by Bayesian estimation method from prior distribution and observation data of said electromagnetic field; and
said step of identifying as a true curved surface on which said current source exists includes the step of
identifying a computer simulated curved surface of which corresponding said posterior probability attains the maximum, among said computer simulated curved surfaces.

13. The computer readable storage medium according to claim 12, wherein
said step of automatically estimating a current distribution includes the step of
identifying a first computer simulated curved surface closest to said brain surface and having posterior probability attaining a relative maximum, among said plurality of computer simulated surfaces, while successively moving from a computer simulated curved surface on the side of the brain surface to a deeper side; and
said step of identifying a curved surface as a true curved surface on which said current source exists includes the steps of
identifying a localized current distribution corresponding to a point of relative maximum of said current distribution, on said first computer simulated curved surface,
separating a plurality of local surfaces each including said localized current distribution, and fixing, among said plurality of local surfaces, local surfaces other than a local surface serving as an object of identification, moving said local surface as an object of identification in the depth direction, and identifying positions where said posterior probability attains the relative maximum, successively from the side closer to said brain surface.

14. The computer readable storage medium according to claim 13, wherein in said step of automatically estimating a current distribution, said current distribution is estimated with a first spatial resolution;

said method further comprising the step of re-estimating said current distribution with a second spatial resolution higher than said first resolution and resolution of said plurality of computer simulated curved surfaces in the depth direction being improved.

15. The computer readable storage medium according to claim 11, wherein said step of setting a hierarchical prior includes the step of setting the hierarchical prior distribution using observation data obtained by other observation method independent of said observation of electromagnetic field for said estimation of the current source.

* * * * *